(12) United States Patent
Hodgson et al.

(10) Patent No.: US 10,327,818 B2
(45) Date of Patent: Jun. 25, 2019

(54) METHOD AND APPARATUS FOR THE TREATMENT OF SCOLIOSIS

(71) Applicant: Bruce Francis Hodgson, Dunedin (NZ)

(72) Inventors: Bruce Francis Hodgson, Dunedin (NZ); Iain Alexander McMillan, Christchurch (NZ); Paul John Morrison, Christchurch (NZ); Simon John Davis, Christchurch (NZ)

(73) Assignee: Bruce Francis Hodgson, Dunedin (NZ)

( * ) Notice: Subject to any disclaimer, the term of this patent is extended or adjusted under 35 U.S.C. 154(b) by 0 days.

(21) Appl. No.: 15/458,462

(22) Filed: Mar. 14, 2017

(65) Prior Publication Data

US 2017/0181771 A1    Jun. 29, 2017

Related U.S. Application Data

(63) Continuation-in-part of application No. 14/405,462, filed as application No. PCT/IB2013/054826 on Jun. 13, 2013, now abandoned.

(30) Foreign Application Priority Data

Jun. 18, 2012   (NZ) ........................................ 600694

(51) Int. Cl.
*A61B 17/70*     (2006.01)
*A61B 17/88*     (2006.01)

(52) U.S. Cl.
CPC ...... *A61B 17/7019* (2013.01); *A61B 17/7034* (2013.01); *A61B 17/7035* (2013.01)

(58) Field of Classification Search
CPC ............ A61B 17/7019; A61B 17/7034; A61B 17/7035

(Continued)

(56) References Cited

U.S. PATENT DOCUMENTS 4,854,304 A    8/1989  Zielke
5,387,212 A    2/1995  Yuan
(Continued)

FOREIGN PATENT DOCUMENTS

EP    0677277    2/1996
NZ    546110    4/2009
(Continued)

*Primary Examiner* — Pedro Philogene
*Assistant Examiner* — David C Comstock
(74) *Attorney, Agent, or Firm* — Holzer Patel Drennan, P.C.

(57) ABSTRACT

A spinal adjustment system which includes at least three implant modules, wherein each implant module includes:
  an engagement apparatus for engaging the implant module with a vertebra; and
  a semirigid, resilient elongated force application means which in use is secured to said engagement apparatus and extends from one implant module to the or each adjacent implant module;
wherein:
said force application means in use engages said the or each adjacent implant module such that said force application means can slide relative thereto in the plane of the force application means;
each force application means in use applies a lifting force to the corresponding implant module and said at least three implant modules together in use apply a rotational force to said system; and
the force application means extending from one implant module to an adjacent implant module extends alongside the force application means extending from said adjacent implant module to said one implant module.

17 Claims, 19 Drawing Sheets

(58) Field of Classification Search
USPC ....... 606/255, 257, 259, 260, 261, 264–267, 606/270, 276
See application file for complete search history.

(56) References Cited

U.S. PATENT DOCUMENTS

| | | | |
|---|---|---|---|
| 5,437,669 | A | 8/1995 | Yuan |
| 5,466,238 | A | 11/1995 | Lin |
| 5,507,746 | A | 4/1996 | Lin |
| 5,613,968 | A | 3/1997 | Lin |
| 5,716,356 | A | 2/1998 | Biedermann |
| 5,899,905 | A | 5/1999 | Errico |
| 5,938,663 | A | 8/1999 | Petreto |
| 6,355,038 | B1 | 3/2002 | Pisharodi |
| 6,355,039 | B1 | 3/2002 | Troussel |
| 6,595,992 | B1 | 7/2003 | Wagner, II |
| 6,613,050 | B1 | 9/2003 | Wagner |
| 6,669,697 | B1 | 12/2003 | Pisharodi |
| 6,802,844 | B2 * | 10/2004 | Ferree ................ A61B 17/7005 606/258 |
| 7,104,992 | B2 | 9/2006 | Bailey |
| 7,220,262 | B1 | 5/2007 | Hynes |
| 7,285,121 | B2 | 10/2007 | Braun |
| 7,632,292 | B2 | 12/2009 | Sengupta |
| 7,686,814 | B2 | 3/2010 | Lim |
| 7,862,586 | B2 | 1/2011 | Malek |
| 8,012,177 | B2 | 9/2011 | Jackson |
| 8,012,182 | B2 | 9/2011 | Couedic |
| 8,043,339 | B2 | 10/2011 | Hudgins |
| 8,092,500 | B2 | 1/2012 | Jackson |
| 8,097,024 | B2 | 1/2012 | Winslow |
| 8,105,368 | B2 | 1/2012 | Jackson |
| 8,366,745 | B2 | 2/2013 | Jackson |
| 8,394,133 | B2 | 3/2013 | Jackson |
| 8,425,567 | B2 | 4/2013 | Niinomi |
| 8,475,498 | B2 | 7/2013 | Jackson |
| 8,496,688 | B2 | 7/2013 | Wang |
| 8,591,560 | B2 | 11/2013 | Jackson |
| 9,011,498 | B2 | 4/2015 | Ogilvie |
| 9,034,015 | B2 | 5/2015 | Karnezis |
| 9,216,039 | B2 | 12/2015 | Jackson |
| 9,241,739 | B2 | 1/2016 | Mueller |
| 2002/0007184 | A1 | 1/2002 | Ogilvie |
| 2003/0065328 | A1 | 4/2003 | Shevtsov |
| 2003/0144665 | A1 | 7/2003 | Munting |
| 2005/0096654 | A1 | 5/2005 | Lin |
| 2006/0079896 | A1 | 4/2006 | Kwak |
| 2006/0155279 | A1 | 7/2006 | Ogilvie |
| 2006/0189983 | A1 | 8/2006 | Fallin |
| 2006/0217715 | A1 | 9/2006 | Serhan |
| 2006/0282074 | A1 | 12/2006 | Renaud |
| 2007/0032123 | A1 | 2/2007 | Timm |
| 2007/0167946 | A1 | 7/2007 | Triplett |
| 2007/0173828 | A1 | 7/2007 | Firkins |
| 2007/0270810 | A1 | 11/2007 | Sanders |
| 2007/0270836 | A1 | 11/2007 | Bruneau |
| 2008/0015577 | A1 | 1/2008 | Loeb |
| 2008/0097441 | A1 | 4/2008 | Hayes |
| 2008/0221620 | A1 | 9/2008 | Krause |
| 2008/0262552 | A1 | 10/2008 | Kim |
| 2008/0269804 | A1 | 10/2008 | Holt |
| 2008/0306513 | A1 | 12/2008 | Winslow |
| 2008/0306525 | A1 | 12/2008 | Mitchell |
| 2009/0012565 | A1 * | 1/2009 | Sachs ................ A61B 17/7041 606/246 |
| 2009/0062860 | A1 | 3/2009 | Frasier |
| 2009/0062861 | A1 | 3/2009 | Frasier |
| 2009/0105755 | A1 | 4/2009 | Capote |
| 2009/0105756 | A1 | 4/2009 | Richelsoph |
| 2009/0222042 | A1 | 9/2009 | Firkins |
| 2009/0259254 | A1 | 10/2009 | Pisharodi |
| 2009/0264931 | A1 | 10/2009 | Miller |
| 2010/0036427 | A1 | 2/2010 | Winslow |
| 2010/0057126 | A1 | 3/2010 | Hestad |
| 2010/0125302 | A1 | 5/2010 | Hammill, Sr. |
| 2010/0137911 | A1 | 6/2010 | Dant |
| 2010/0198260 | A1 | 8/2010 | Gabelberger |
| 2010/0268279 | A1 | 10/2010 | Gabelberger |
| 2010/0331884 | A1 | 12/2010 | Hestad |
| 2011/0077687 | A1 * | 3/2011 | Thompson ......... A61B 17/7004 606/254 |
| 2011/0245883 | A1 * | 10/2011 | Dall ................ A61B 17/7035 606/305 |
| 2012/0029567 | A1 | 2/2012 | Zolotov |
| 2012/0109211 | A1 | 5/2012 | Braunschweiler |
| 2013/0090691 | A1 * | 4/2013 | Zhang ................ A61B 17/7001 606/264 |
| 2013/0184762 | A1 | 7/2013 | Harper |
| 2014/0018858 | A1 | 1/2014 | Laeng |
| 2015/0230830 | A1 | 8/2015 | Frankel |

FOREIGN PATENT DOCUMENTS

| | | |
|---|---|---|
| WO | 97035529 | 10/1997 |
| WO | 2008089096 | 1/2001 |

* cited by examiner

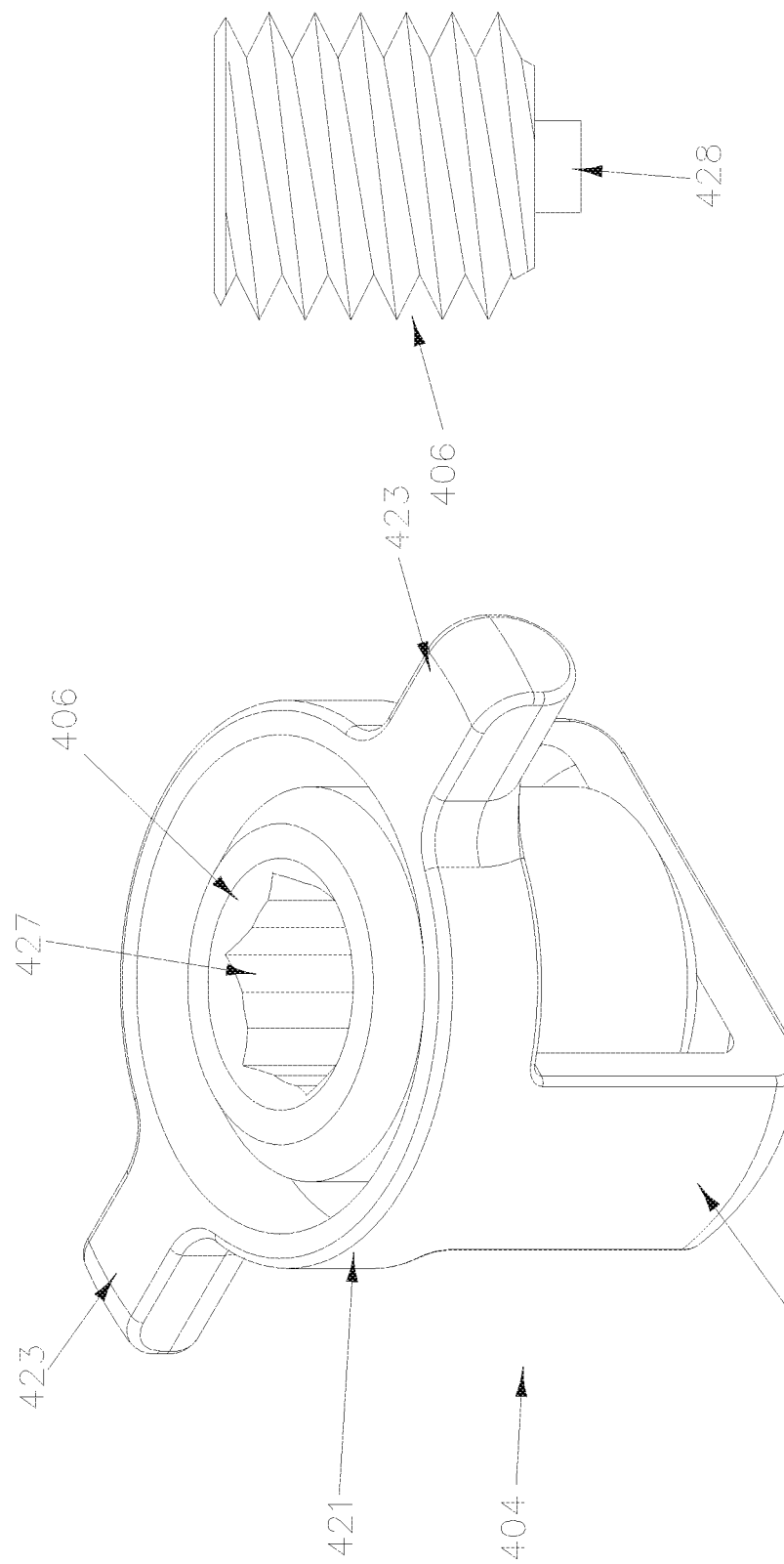

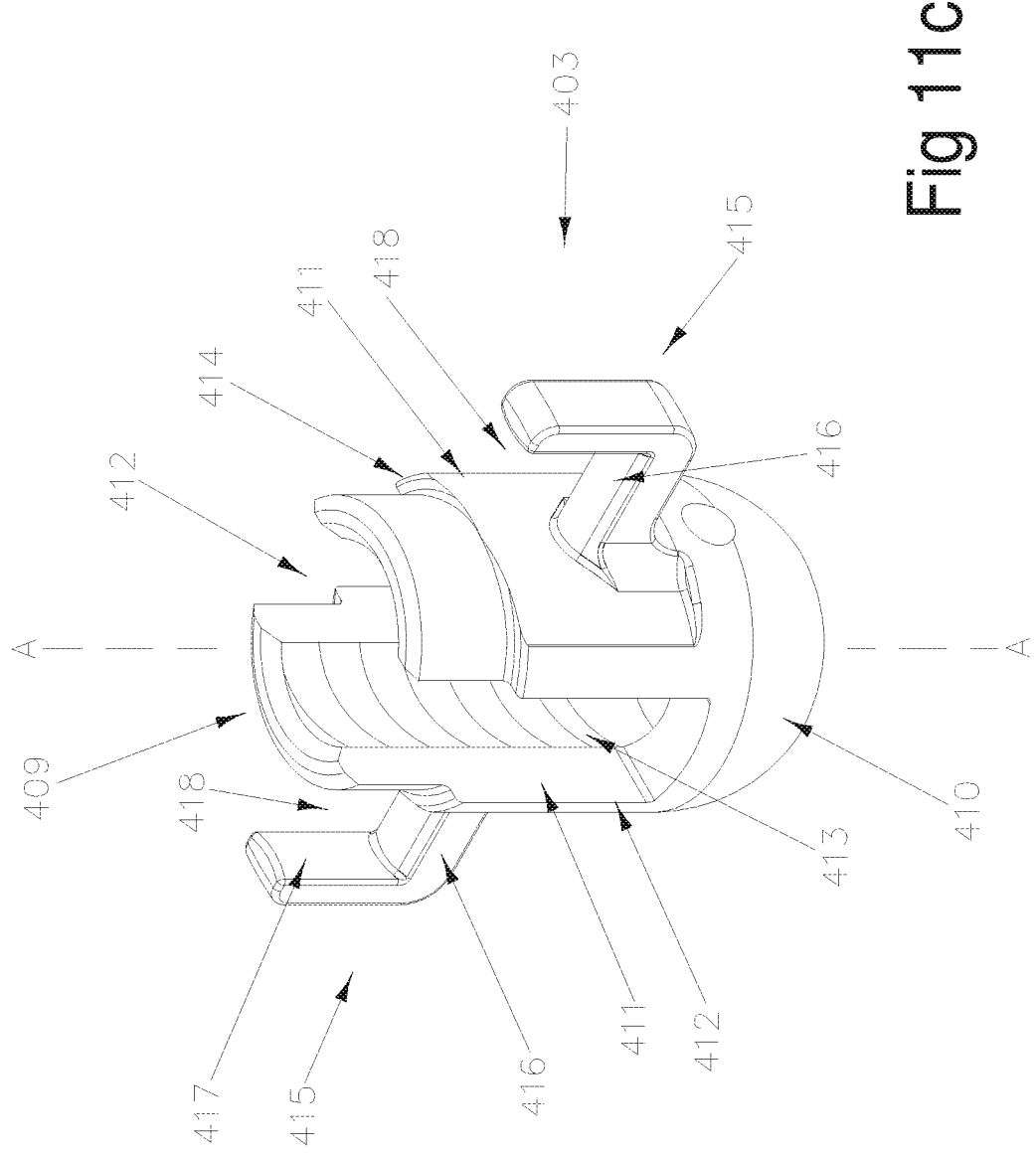

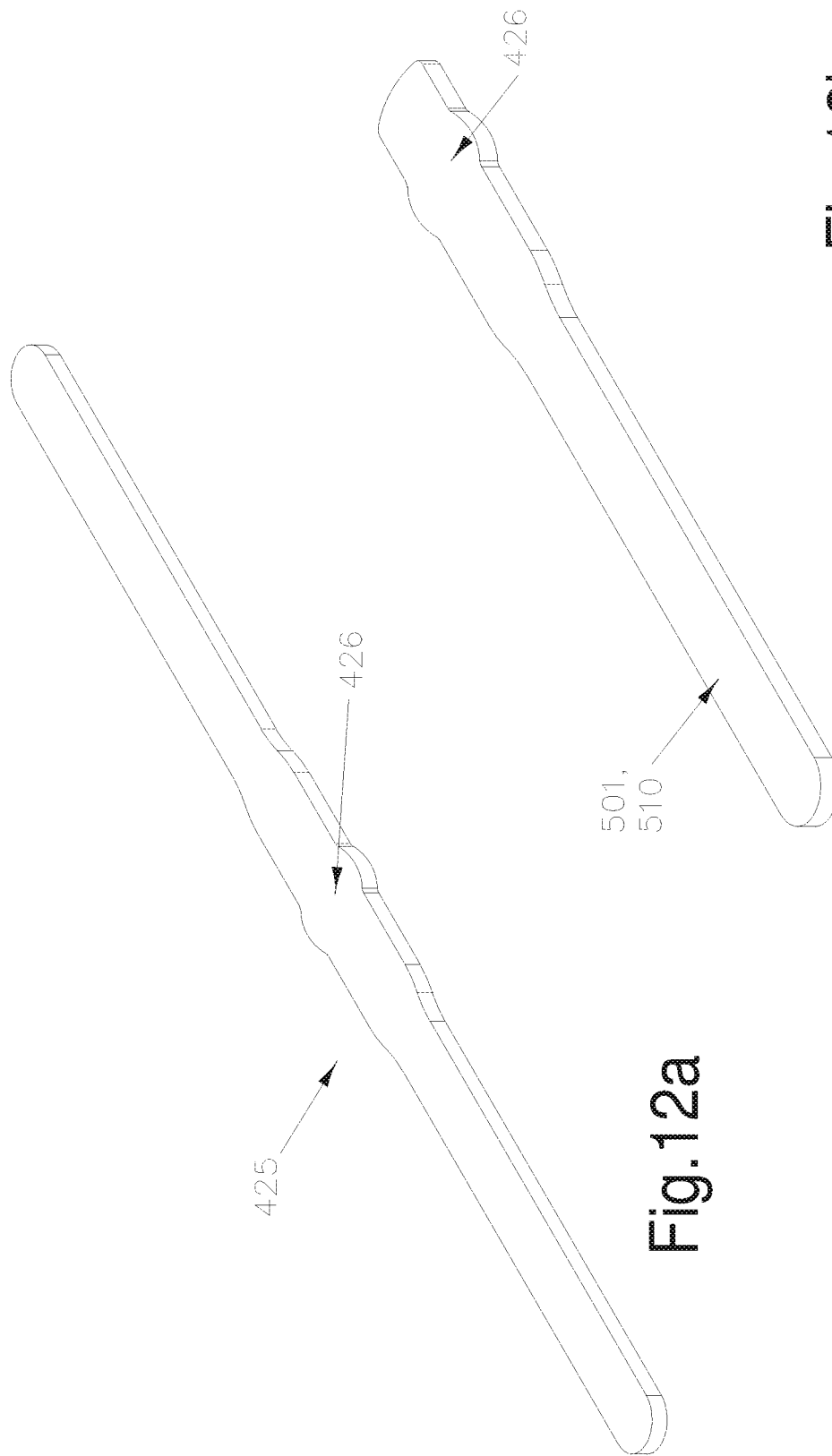

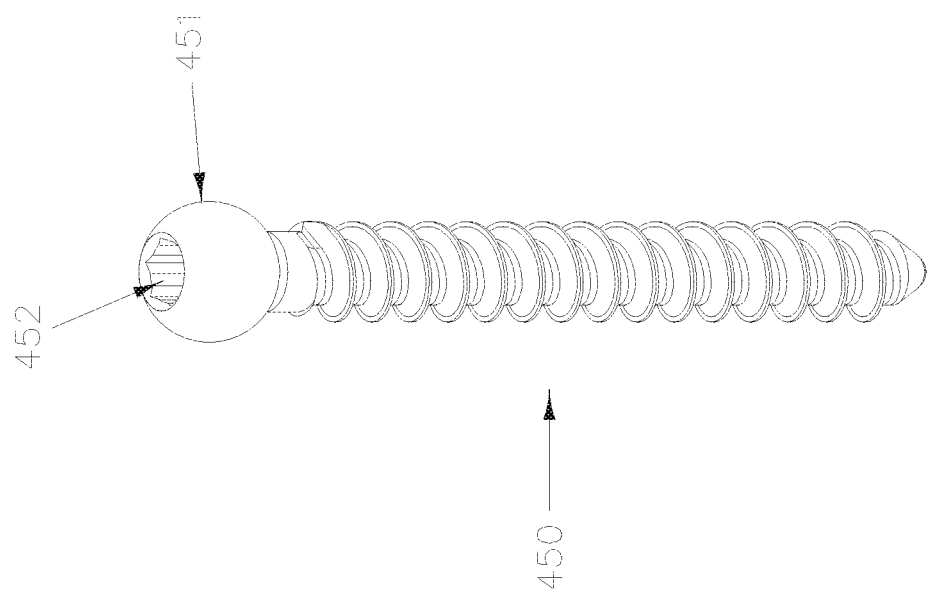

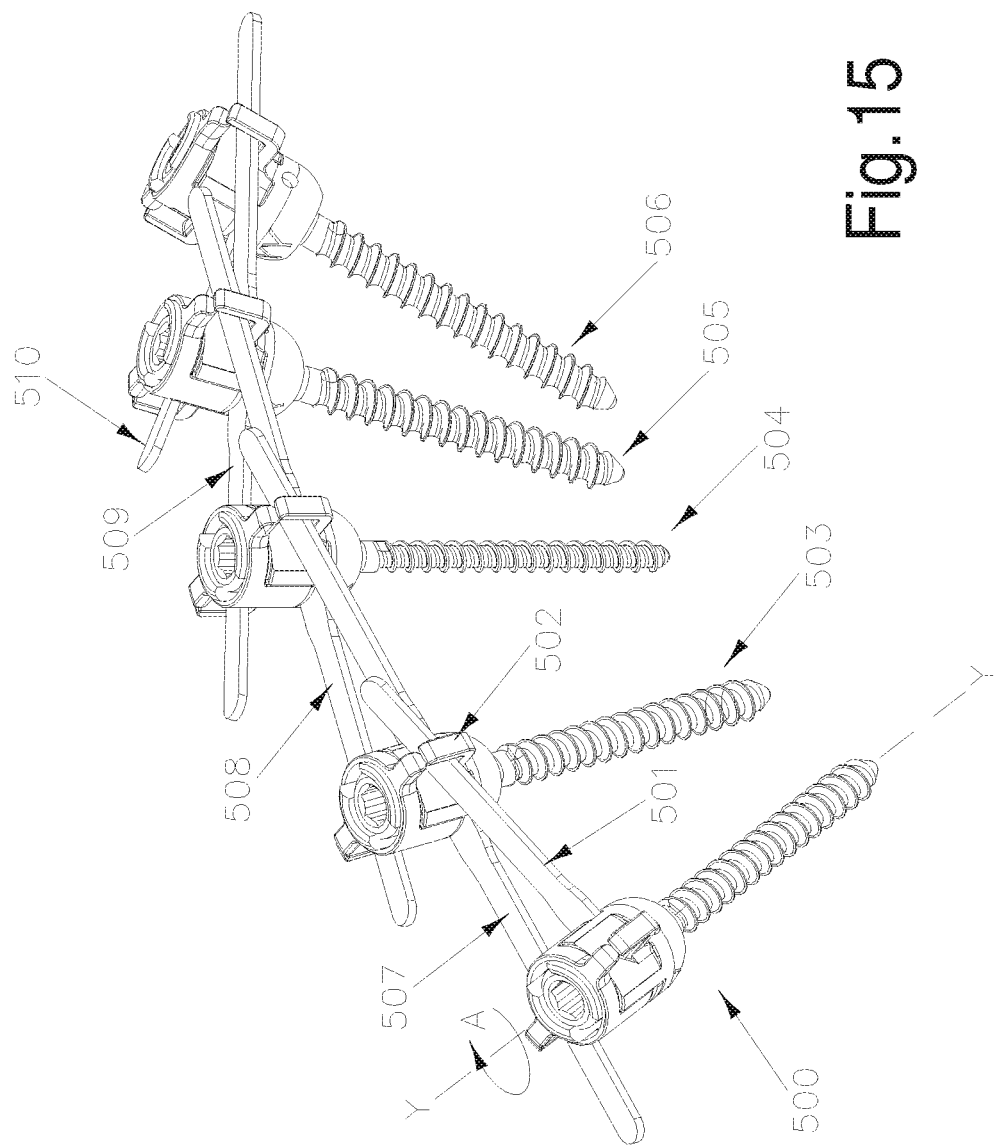

METHOD AND APPARATUS FOR THE TREATMENT OF SCOLIOSIS

CROSS REFERENCE TO RELATED APPLICATIONS

This application is a continuation-in-part of U.S. patent application Ser. No. 14/405,462 entitled "METHOD AND APPARATUS FOR THE TREATMENT OF SCOLIOSIS," filed on Dec. 4, 2014, which is a 371 National Stage Filing of International App. No. PCT/IB2013/054826 filed on Jun. 13, 2013, entitled "METHOD AND APPARATUS FOR THE TREATMENT OF SCOLIOSIS," the contents of which are incorporated by reference herein as if set forth in full.

FIELD OF THE INVENTION

The present invention is a method of treatment of scoliosis and similar spinal conditions, and an apparatus for applying this new method. As used herein, the term "a similar spinal conditions" refers to conditions in which the spine is deformed in some manner. For example, the apparatus and method of the present invention may be used for the reduction of a spondylolisthetic vertebra, or for creating a lordosing force for the correction of kyphotic deformities, for example Scheuremann's Kyphosis, or for other conditions.

BACKGROUND

Any discussion of the prior art throughout the specification is not an admission that such prior art is widely known or forms part of the common general knowledge in the field.

Scoliosis is a medical condition in which a person's spine has a deformity which causes the spine to be primarily curved from side to side; it may also be rotated along its axis. On an x-ray, when taken from the front or back of the spine of an individual with a typical scoliosis, the spine may take the form of an "S" or a "C" rather than a straight line. It is typically classified as congenital (caused by vertebral anomalies present at birth), idiopathic (sub-classified as infantile, juvenile, adolescent, or adult according to when onset occurred) or as having developed as a secondary symptom of another condition, such as cerebral palsy, spinal muscular atrophy or due to physical trauma.

Scoliotic curves greater than 10° affect 2-3% of the population of the United States. According to the US National Scoliosis Foundation, scoliotic curves greater than 20° affect about one in 2500 people. Curves convex to the right are more common than those to the left, and single or "C" curves are slightly more common than double or "S" curve patterns. Males are more likely to have infantile or juvenile scoliosis, but there is a high female predominance of adolescent scoliosis.

The prognosis of scoliosis depends on the likelihood of progression. The general rules of progression are that larger curves carry a higher risk of progression than smaller curves, and that thoracic and double primary curves carry a higher risk of progression than single lumbar or thoracolumbar curves. In addition, patients who have not yet to reached skeletal maturity have a higher likelihood of progression.

Pain is often common in adulthood, especially if the scoliosis is left untreated. Spinal surgery may be performed to stabilize curvature and prevent worsening, therefore improving the patient's quality of life. It should be noted that the surgery does not necessarily result in pain loss.

The underlying cause of scoliosis is not well understood. However, one theory is that the left to right curvature can develop as the growing body attempts to compensate for an abnormal front to back curvature. A "normal" mature spine is curved and includes a top area of lordosis (an arc pulling the head back and up), a mid area of kyphosis (a hunching curve forwards) and a lower area of lordosis. The net result of these curved areas is to position the head above the pelvis, for stability. These areas of curvature are caused by the wedge shapes of adjacent vertebrae in the spinal column, which locally tilt the spine in a forward or backward direction. However, where at least one vertebra is not sufficiently wedge-shaped, but too rectangular, the spine does not curve normally at that point. This most frequently results in insufficient kyphosis in the central part of the spine. According to one theory, scoliosis can develop when the body, attempting to add kyphosis, introduces a curvature in the perpendicular plane.

As noted above, scoliosis typically is diagnosed in children or adolescents, usually before full progression of the condition. Since the disease does not progress to a dangerous extent in 95% of sufferers, conventional treatment (which is outlined below) may be delayed until it is certain it will be needed.

The conventional treatment options for scoliosis are:
1. Observation
2. Bracing
3. Surgery Observation is simply monitoring of the patient over time to determine if their condition is declining or stabilising.

Bracing is only done when the patient has bone growth remaining, and is generally implemented in order to hold the curve and prevent it from progressing to the point where surgery is necessary. Bracing involves fitting the patient with a device that covers the torso and in some cases extending to the neck. The effectiveness of bracing differs depending on the compliance of the patient, the type of brace used and on the individual scoliosis.

Surgery is usually indicated for curves that have a high likelihood of progression, curves that cause a significant amount of pain with some regularity, curves that would be cosmetically unacceptable as an adult, curves in patients with spina bifida and cerebral palsy that interfere with sitting and care, and curves that affect physiological functions such as breathing.

Known systems incorporating tethers or telescoping rods correct spinal deformity in one plane only, that of the restricting action provided by the construct or imparted by a corrective force applied, and do not fully correct a three-dimensional deformity. These systems may not allow the patient to retain a full range of motion.

Spinal fusion is the most widely performed surgery for the treatment of scoliosis and it is an irreversible procedure. In this procedure, spinal instrumentation (screws, hooks and rods) and bone grafts are utilized to link the vertebrae so that as the spine heals the vertebral bodies will become one solid bone mass and the vertebral column becomes rigid. This prevents worsening of the curve, but at the expense of spinal movement.

The purpose of the spinal instrumentation (screws, hooks and rods) is twofold. First, it enables the surgeon to adjust and reduce the curvature to some degree. The second purpose the instrumentation fulfils is to hold the spine still so that the grafted bone and vertebrae fuse into a solid bone mass, which can take up to a year or more to occur for adults. Once the fusion is solid, the instrumentation has done its job and may be removed, although it is usually left in place. If a solid fusion is not achieved, the instrumentation will eventually fatigue and fail and the patient will most likely experience pain at the spinal levels which have failed to fuse.

Spinal fusion is typically only carried out when the patient has reached, or is close to, skeletal maturity, as a fused spine cannot grow in length. The procedure involves an operation typically taking about 8 hours, with a number of associated risks. The result of this treatment enables the patient to survive, but with a severely limited range of movement, since they cannot flex their spine to bend over or to the side.

SUMMARY OF THE INVENTION

It is an object of the present invention to provide an alternative method for treatment of scoliosis and similar spinal conditions and an apparatus for enabling the method. The invention may also provide a treatment and apparatus suitable for use in patients who may have not achieved skeletal maturity, and/or whose condition has not yet progressed but are identified as disposed to a dangerous progression.

The present invention provides a spinal adjustment system which includes at least three implant modules, wherein each implant module includes:
- an engagement apparatus for engaging the implant module with a vertebra;
- a semirigid, resilient elongated force application means which in use is secured to said engagement apparatus and extends from one implant module to the or each adjacent implant module;

wherein:
- said force application means in use engages said the or each adjacent implant module such that said force application means can slide relative thereto in the plane of the force application means;
- each force application means in use applies a lifting force to the corresponding implant module and said at least three implant modules together in use apply a rotational force to said system;
- the force application means extending from one implant module to an adjacent implant module extends alongside the force application means extending from said adjacent implant module to said one implant module.

The present invention further provides implant module for use in the spinal adjustment system, wherein said implant module includes:
- an engagement apparatus for engaging the implant module with a vertebra;
- a semirigid, resilient elongated force application means which in use is secured to said engagement apparatus and is arranged to extend outwards from said module so as to be engageable with an adjacent module;
- a pair of opposed receiving means each arranged to slidably receive an end of said force application means.

Preferably, said engagement apparatus is rigidly or pivotably secured to a cage for receiving and supporting said force application means, said cage having said pair of opposed receiving means rigidly secured thereto.

Preferably also, said cage is internally screw threaded and is formed with a pair of opposed slots dimensioned such that said force application means is receivable within said cage with at least one end of said force application means extending outwards from said module; and wherein said module further includes a reinforcing sleeve which is dimensioned to be an easy sliding fit over said cage and provides a U shaped yoke having side portions positioned and dimensioned to close off said opposed slots, and a base portion which overlies the portion of said force application means within said cage.

Preferably also, the module further includes a retainer formed with an internal bore for receiving a driving tool, said retainer being externally screw threaded to engage the internal screw thread on the cage, such that when the retainer is screwed into the cage, the retainer, reinforcing sleeve, and force application means all are rigidly secured together. The reinforcing sleeve may also provide a pair of opposed projections which are positioned so as to overlie said pair of opposed receiving means when said sleeve is positioned on said cage.

Preferably, the engagement apparatus engaging each implant module with the corresponding vertebra is a pedicle screw or a pedicle hook, most preferably a pedicle screw which is either rigidly or pivotably secured to a cage for receiving and supporting the force application means. In the embodiment where the pedicle screw is pivotably secured to a cage, there is also provided means for locking the angle between said pedicle screw and said cage.

Preferably, the force application means is a leaf spring or a rod or a bar. Preferably also, the force applied by the force application means is adjustable by altering the dimensions and/or the proportions of said means. However, in one embodiment, the force applied by the force application means is also adjustable by means of a spring tensioner.

The present invention also provides a method for adjusting the alignment of the spine, including the steps of:
- providing a spinal adjustment system as described above;
- engaging each implant module with a vertebra in the part of the spine to be realigned, by means of said engagement apparatus;
- engaging the force application means of each implant module with the or each adjacent implant modules, such that each force application means applies a lifting force to the corresponding implant module, and said at least three implant modules together apply a rotational force to the associated part of the spine.

The present invention further provides for the use of the spinal adjustment system described above for the treatment of a condition selected from the list consisting of: scoliosis, spondylolisthetic vertebra and Scheuermann's Kyphosis.

The proposed system is based on the concept that rather than using traditional spinal instrumentation to attempt to forcibly correct the deformity during one procedure and then fusing the spine in the position achieved, the proposed instrumentation system would instead correct the deformity over a period of time through the application of "small" forces while still allowing motion of the spine. The term "small" force means that the force is small and gentle compared to the forces used in the single-procedure correction traditionally used.

All of the embodiments described will allow the patient some degree of spinal motion.

This is a similar concept to that used in modern orthodontics where braces apply small forces to the teeth in order to cause realignment of the teeth, as opposed to older brace systems which apply a large load to the teeth at the time of treatment causing an initial correction to occur with no significant correction thereafter, until the next adjustment of the bias occurs.

The intent of this system is that only a 'gentle' corrective force would be applied to the vertebral bodies rather than the application of large forces as is currently required in order to realign the spine during a spinal fusion procedure. Thus, in a similar way to which braces work in orthodontics, these gentle forces would over time cause 'realignment' of the vertebral bodies.

As the vertebral bodies start to become 'realigned' the springs will return to their unloaded rest state, thus reducing the spring force applied to the vertebral bodies and helping to prevent over correction of the scoliosis deformity.

The implant modules work by each applying force to a vertebra relative to the adjacent superior and inferior vertebrae. This force causes lifting, translation and rotation of the vertebra relative to its superior and inferior neighbours, i.e., each vertebra is not only rotated towards the correct position, but also is lifted, to facilitate this rotation. By continued coupling of the implant modules, this pattern is repeated along the length of the system of implant modules (which preferably extends along the extent of the spinal deformity), with the implant modules becoming the fixed reference points, and all the intermediate vertebrae being lifted, translated and rotated relative to these end points, and their engaged neighbours. This allows for correction of the deformity over time, while maintaining full natural motion at all spinal levels and allowing for growth of the patient.

The implant modules would preferably be implanted during one procedure and require no further surgical intervention, but further surgical procedures to adjust, add to, or reduce the implant construct could be accommodated, if required.

Once correction has occurred, the surgeon may chose to leave the implant system in place for some time, allowing for remodelling of the bone and soft tissues to accommodate the new spinal state. Removal too early may result in further progression of the scoliosis. In orthodontics correction occurs within three months, but braces are left in place a further nine months, to allow for stabilisation. The decision will be made by medical to advisors on a case-by-case basis.

A number of advantages are anticipated for this system including:
1. The patient's spine would not be fused in order to correct the scoliotic deformity. Instead the patient would retain full motion (flexion, extension, lateral bending, twisting and growth) at each spinal level while the correction of the scoliotic curve was achieved slowly over time. As such, the patient will potentially not have any of the issues associated with spinal fusion.
2. It may be possible to achieve a better correction of the scoliosis deformity, as all of the spinal anatomy (musculature, ligaments, etc) would have time to adapt to the correction. In much as the same way this anatomy remodels to a deformed state as the patient's scoliosis progresses, these same structures will have time to remodel to a less deformed state as the deformity is corrected. This may provide an advantage over spinal fusion surgery.
3. As the spine has retained full motion and the spinal anatomy would have time to remodel using the proposed system, the result may be a full functional spine with the scoliosis deformity corrected. Therefore once the patient has reached skeletal maturity and the likelihood of the scoliosis deformity re-occurring and/or progressing had decreased sufficiently, it may be possible to remove the whole implant.
4. A limiting factor for spinal fusion is that it is preferable to wait until the patient has reached or is close to reaching skeletal maturity, otherwise the spinal fusion will cause restriction in their growth. Clearly this has to be balanced against the progression of the scoliosis and associated problems. However the proposed system does not result in the spine being fused, so that growth of the spine can still occur. This potentially allows for early treatment of scoliotic spines for patients whose condition is known to progress, using less aggressive hardware and corrective forces—thus arresting any scoliosis progression and potentially correcting any deformity already present, at a younger age. This presents a significant advantage particularly where the patient's condition has been indicated (through genetic testing or similar) as being likely to progress.
5. The operation required to insert the apparatus of the present invention is considerably less invasive, and less likely to damage the spine, than the conventional spinal fusion techniques.

It should be noted that all of the components of the apparatus the present invention are made of a biologically inert, sterilisable material which is suitable for implantation in a live host, such as titanium or a suitable titanium alloy.

BRIEF DESCRIPTION OF DRAWINGS

By way of example only, preferred embodiments of the present invention are described in detail below with reference to the accompanying drawings, in which:

FIG. 4b is an isometric view of the series of implant modules shown in FIG. 4a;

FIGS. 11a-11d inclusive are isometric views of some of the components of the module of FIG. 11, on a larger scale;

FIGS. 12a and 12b are isometric views of springs;

FIG. 14 is an isometric view of a component of the variant of FIG. 13; and

FIG. 15 is an isometric view of the fourth embodiment in use; and

BEST METHODS OF CARRYING OUT THE INVENTION

First Preferred Embodiment

Figure 1:
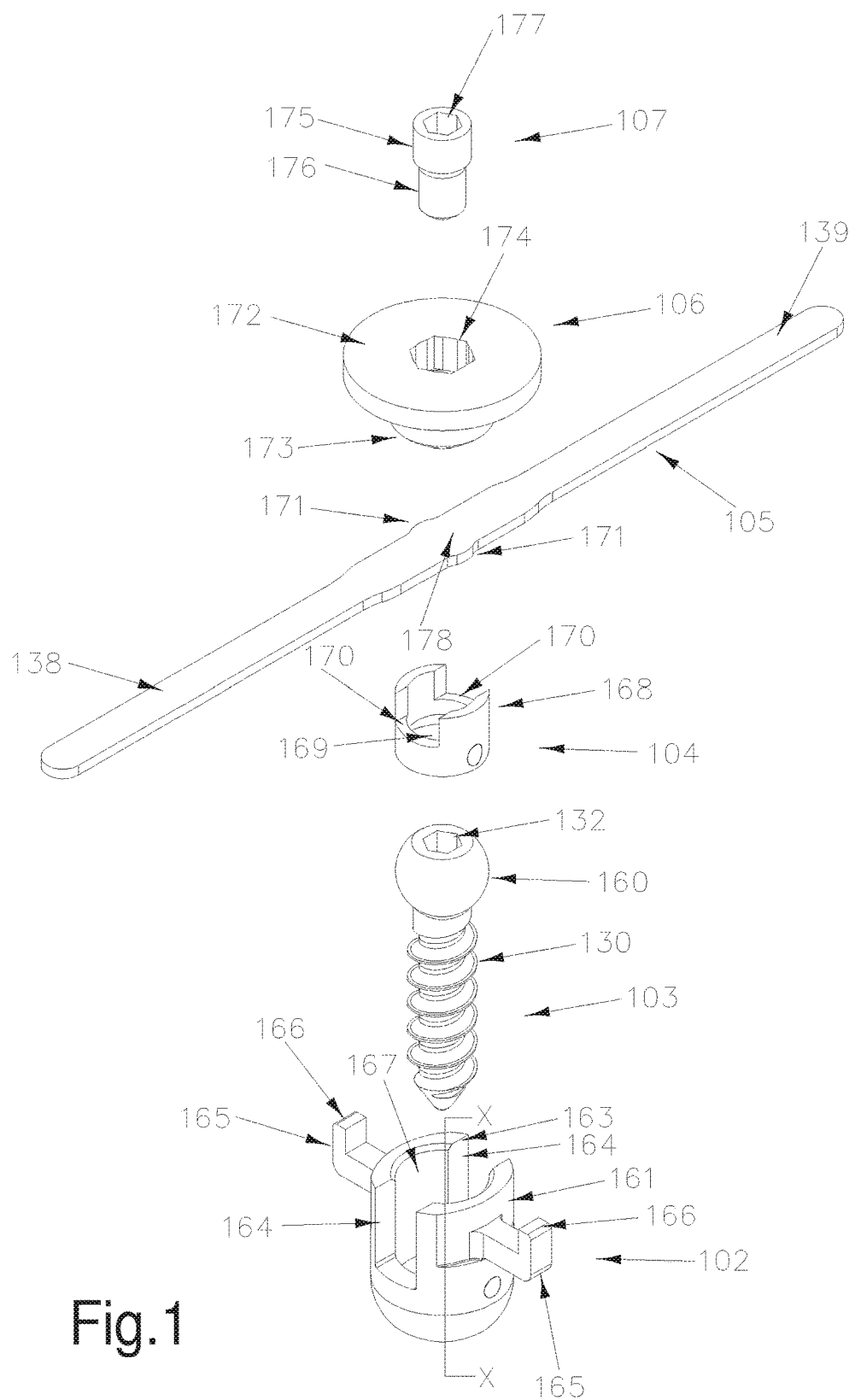
FIG. 1 is an exploded isometric view of a first preferred embodiment of an implant module of the present invention.
Figure 2:
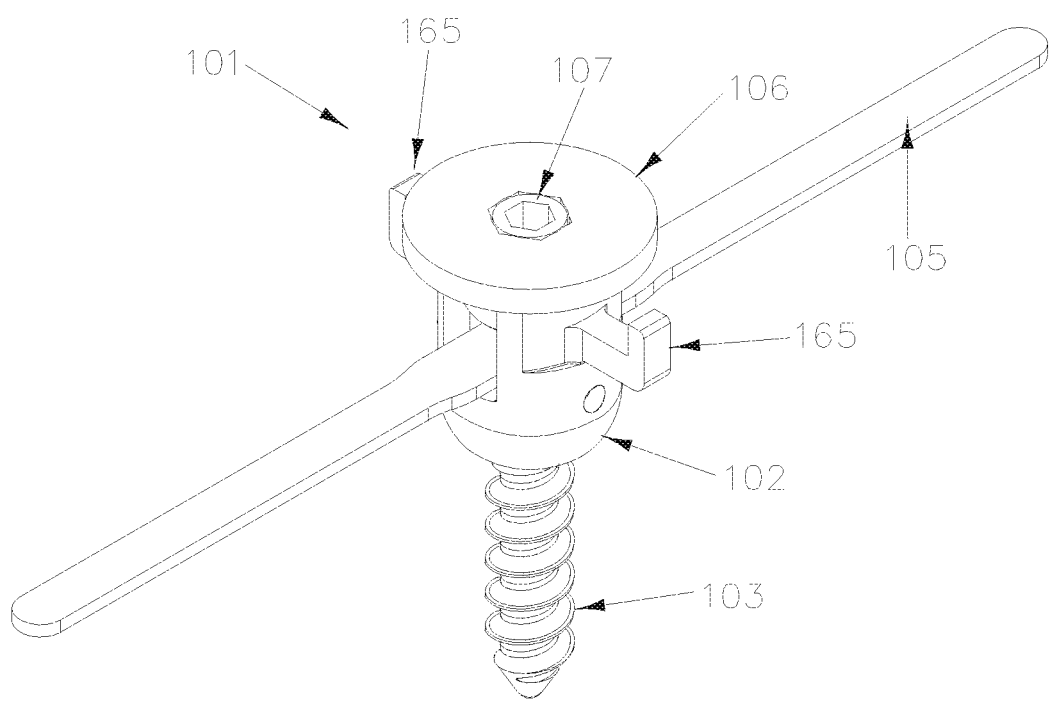
FIG. 2 is an isometric view of the implant module shown in FIG. 1 when assembled.
Figures 3A, 3C:
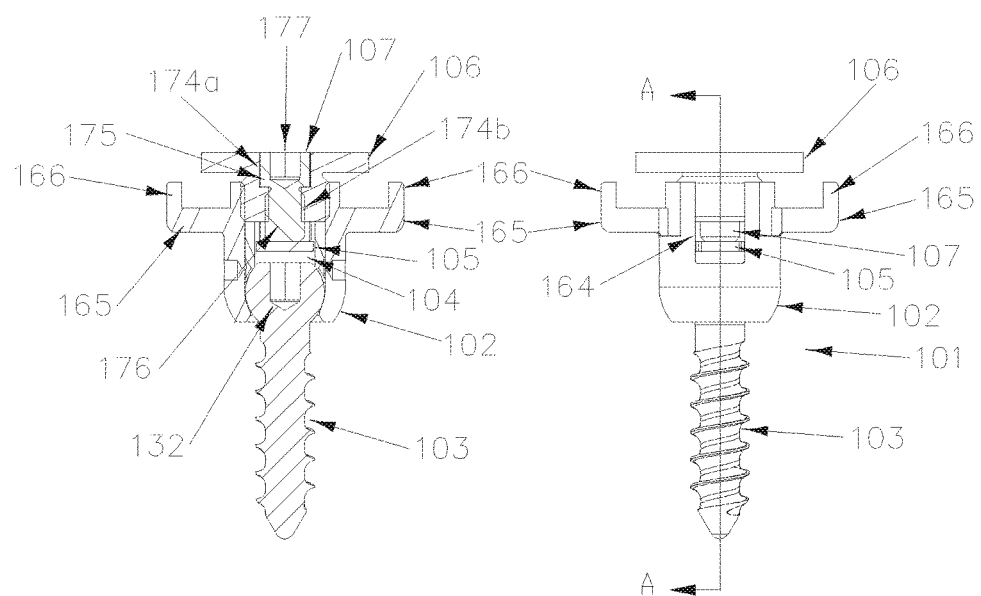
FIG. 3a is a side view of the implant module shown in FIG. 2.
FIG. 3c is a cross-section of the implant module shown in FIG. 3b along the line B-B.
Figure 3B:
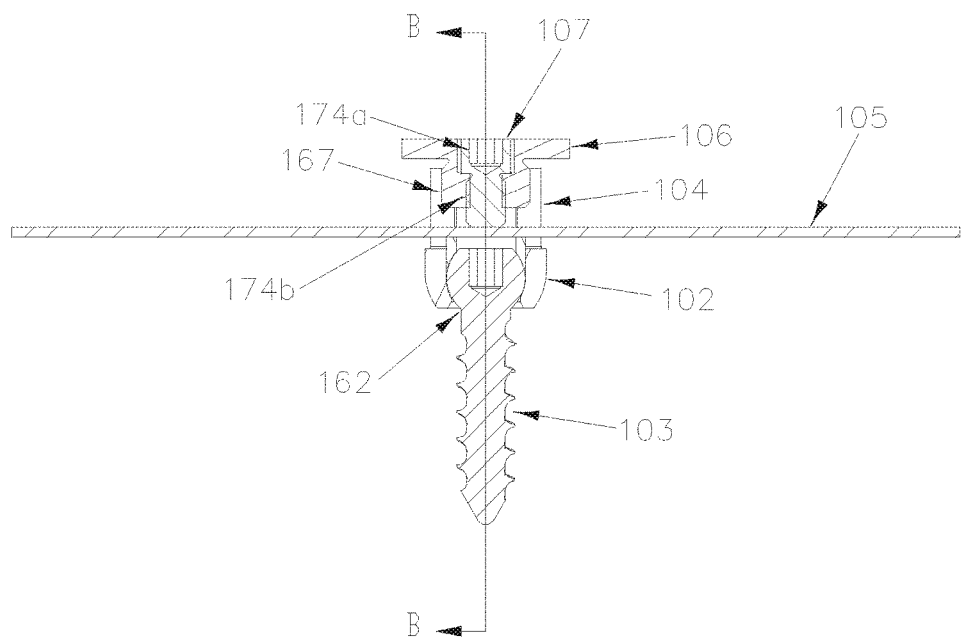
FIG. 3b is a cross-section of the implant module shown in FIG. 3a along the line A-A.

FIGS. 1, 2 and 3 show a first preferred embodiment of an implant module 101 which is part of the apparatus of the present invention.

The implant module 101 includes a cage 102, a pedicle screw 103, a spring socket 104, spring 105, spring cap 106 and tensioner 107.

Pedicle screw 103 is similar to a well-known type including a screw threaded column 130 adapted to engage with a pedicle of a vertebra. At a first end of column 130, a rounded screw head 160 is provided with tool engagement means, preferably in the form of a screw tool cavity 132 adapted to receive a tool, e.g. an Allen key. Engagement of an appropriate known type of tool with these tool engagement means will allow rotation of the screw 103, and therefore engagement of column 130 with a pedicle.

Screw 103 may be similar to any of the many different commercially available spinal screws. In alternative embodiments, the pedicle screws 103 may be replaced with "pedicle hooks" or other known apparatus for engagement with vertebrae.

Cage 102 has an essentially cylindrical cage body 161. A first end of cage body 161 includes a first cage aperture 162 dimensioned to allow screw threaded column 130 of pedicle screw 103 to pass therethrough, but not to allow screw head 160 to pass therethrough. A second cage aperture 163 at a second end of cage body 161 distal to the first end is dimensioned to allow screw head 160 to pass therethrough and extends into the cage body 161 to a depth greater than the height of screw head 160. The first end of cage body 161 may be tapered between the width of second cage aperture 163 and the first cage aperture 162. The sidewall of cage body 161 includes two cage spring slots 164 opposite each other, each cage spring slot 164 extending from the second end of cage body 161 through a significant depth of the cage body sidewall. Extending outwards from opposite sides of cage body 161 are a pair of spring shelves 165. Preferably each of the spring shelves 165 is equidistant from the two cage spring slots 164 around the circumference of the cage body 161. Each spring shelf 165 includes a spring shelf upstand 166 extending approximately parallel to the longitudinal axis X-X of cage body 161. A cage interior wall 167 of cage body 161 includes cap engagement means, preferably a screw-thread (not shown).

Spring socket 104 consists of an essentially cylindrical socket body 168. A socket aperture 169 passing through the entire length of socket body 168 is dimensioned to allow access to screw tool cavity 132 in screw head 160, but not to allow screw head 160 to pass therethrough. The sidewall of socket body 168 includes two socket spring slots 170 opposite each other, each socket spring slot 170 extending through a significant depth of the socket body sidewall.

Spring 105 include a first arm 138 and a second arm 139 extending in opposite directions in a spring plane from an engagement section 178 located partway along the length of spring 105. Engagement section 178 includes a pair of small opposing protrusions 171 dimensioned to complement the interior of socket aperture 169. Although spring 105 is shown as a leaf spring, other forms could be used, such as flexible rods or bars, or contoured and profiled forms, and the springs 105 of different implant modules 101 used m in the apparatus may be of varying thickness and cross-section, so as to exert a predetermined force in use, as described below.

Spring cap 106 includes a cap lid 172 and a cap shaft 173, with a cap aperture 174 extending through both cap lid 172 and cap shaft 173. Cap shaft 173 is dimensioned to fit inside cage body 161, and includes cage engagement means, adapted to engage the cap engagement means of cage body 161, preferably in the form of an external screw thread (not shown) dimensioned to engage the screw threaded cage interior wall 167 of cage body 161. Cap lid 172 is wider than cap shaft 173, and although it is shown in this embodiment as being circular, is may be narrower in one dimension, for example being elliptical or hexagonal in shape. Cap lid 172 includes tool engagement means, which may include external flats and/or a cap tool cavity adapted to receive a tool, e.g. an Allen key. Engagement of an appropriate known type of tool with either of these tool engagement means will allow the engagement of cap shaft 173 with cage 102, for example by rotation of the spring cap 106. In this preferred embodiment, cap lid aperture 174*a* (being the section of cap aperture 174 enclosed by cap lid 172) is in the form of a cap tool cavity. The cap shaft aperture 174*b* (being the section of cap aperture 174 enclosed by cap shaft 173) includes tensioner engagement means, preferably in the form of an internal screw thread.

Tensioner 107 includes a tensioner crown 175 coaxially aligned with a tensioner shaft 176. Tensioner shaft 176 is at least as long as cap shaft aperture 174*b*, and is dimensioned and adapted to engage with the tensioner engagement means contained therein, preferably in the form of an external screw thread. Tensioner crown 175 is dimensioned to fit within cap lid aperture 174*a*, and includes tool engagement means, preferably in the form of a tensioner tool cavity 177 adapted to receive a tool, e.g. an Allen key.

It will be recognised by one skilled in the art that the implant modules must be made of appropriate surgical materials, having the necessary characteristics of ability to be sterilized, biological inertness, strength and flexibility. In particular, different materials and spring geometries used for springs 105 will apply different strengths of spring force, as may be required in a particular case.

Implant modules 101 are used in the method of treatment of the present invention as follows:

Cage 102, pedicle screw 103 and spring socket 104 may be preassembled by passing the column 130 through the second cage aperture 163 and the first cage aperture 161 of cage 102, then inserting spring socket 104 into the second cage aperture 163 of the cage 102.

Screws 103 are screwed into the pedicles of vertebrae along the affected length of the spine, by passing a tool through socket aperture 169 and second cage aperture 163 to engage the screw tool cavity 132 in the screw head 160.

Screws 103 may be engaged with every vertebra, or some may be skipped, depending of the extent of the scoliosis and the desired end result. Screws 103 will usually be engaged with the pedicles on only one side of the spine, but it is envisaged that in particular clinical cases it may be desirable to install implants on both sides of the spine.

The cage 102 on each screw 103 can rotate about the rounded screw head 160 until they are aligned, as shown for example in FIG. 4. Once each screw 103 is in place, the springs 105 are sequentially installed. The engagement section 178 of spring 105 is placed inside the socket aperture 169 so that each of the first arm 138 and the second arm 139 extends from the engagement section 178 through a socket spring slot 170 and a cage spring slot 164. Protrusions 171 are inside the socket aperture 169, limiting the ability for lengthwise translation of the spring 105. Springs 105 having different characteristics may be provided in different implant modules engaged with different vertebrae, allowing the force applied to each vertebra to be deliberately selected to achieve the desired clinical outcome.

Figure 4A:
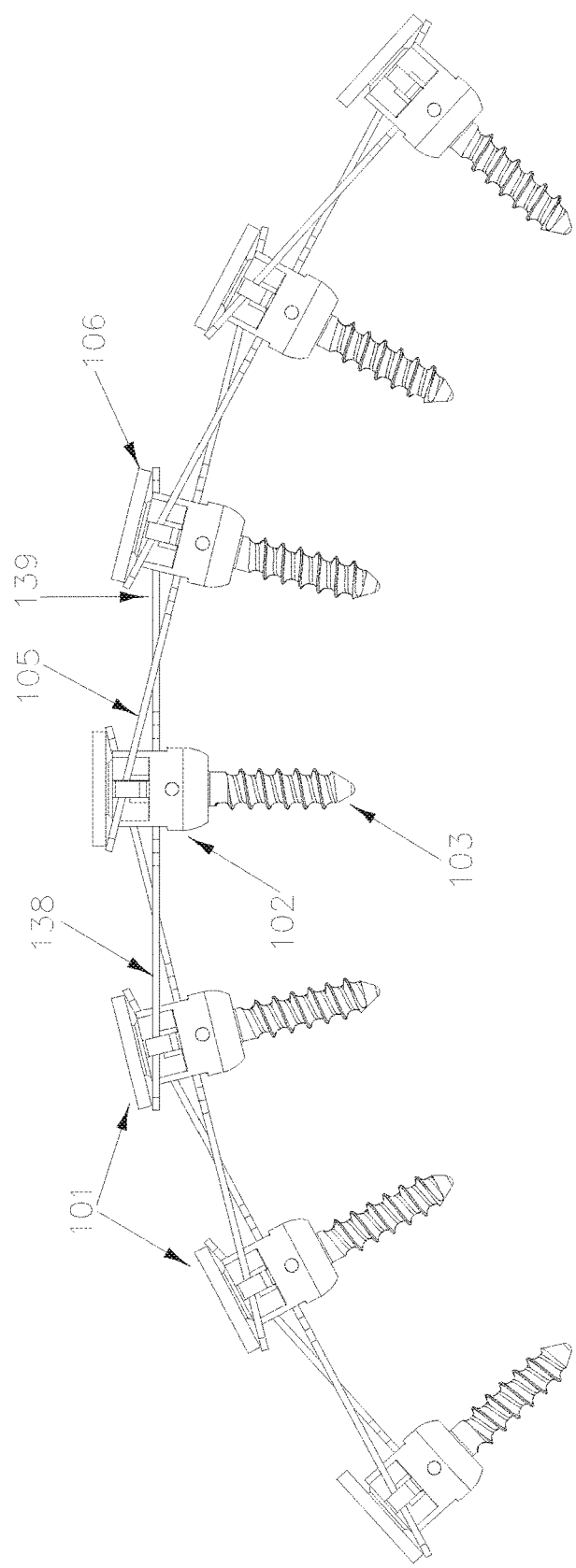
FIG. 4a is a side view of a series of implant modules according to the first preferred embodiment of the present invention.

As shown in FIGS. 4a/b, the first arm 138 of the spring 105 of a first implant module 101 is oriented to rest on a spring shelf 165 of a first adjacent implant module 101. The second arm 139 of the spring 105 of the first implant module 101 is oriented to rest on a spring shelf 165 of a second adjacent implant module 101. The same procedure is followed with the springs associated with each of the implant modules, until each implant module 101 (other than at the two ends), is engaged with two adjacent implant modules 101, one on a superior vertebra, and one on an interior vertebra.

Figure 4B:
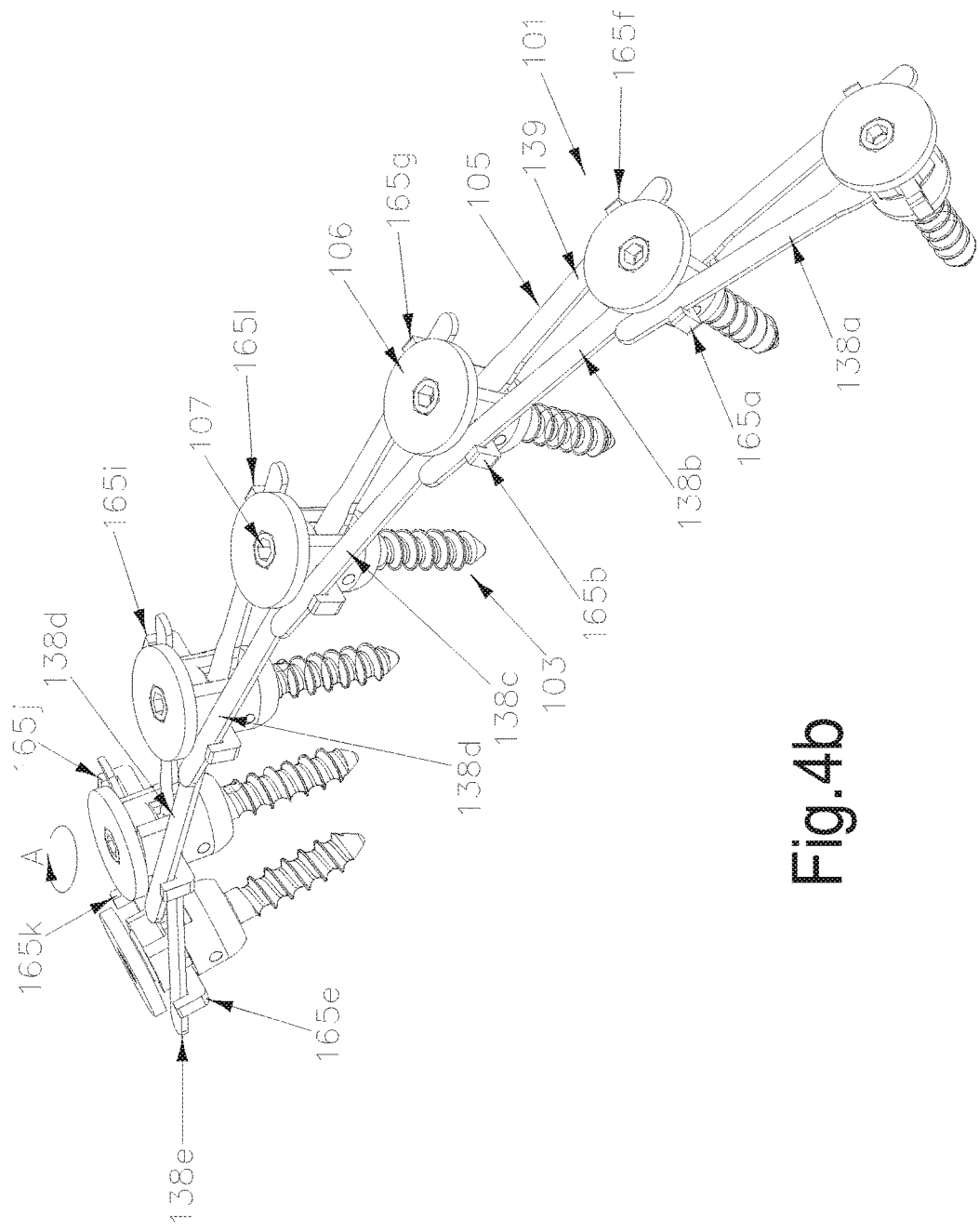

As can be seen in FIGS. 4a and 4b, in respect of vertebrae at the extremal ends of the affected length of spine, a special "one-sided" spring is provided, so that the extremal implant modules are each only engaged with one adjacent implant module 101. The end implant modules may be otherwise identical to the intermediate implant modules.

The cap shaft 173 of a spring cap 106 is then engaged with cage body 161. A tool is engaged with the cap lid aperture 174a to screw the cap shaft 173 into the screw threaded cage interior wall 167 of cage body 161. Spring cap 106 presses spring socket 104 on to the screw head 160, locking the angle of cage 102 relative to the screw threaded column 130 of screw 103. Spring cap 106 also holds spring 105 of that implant module 101 in its position inside spring socket 104.

When spring cap 106 is thus engaged with the cage 102, the cap lid 172 extends over each of the spring shelves 165 of that implant module 101. If the cap lid 172 is asymmetrical, the narrower dimension is oriented in the inferior-superior direction. Thus, the second arm 139 of the spring 105 of the first adjacent implant module 101 is enclosed by a spring shelf 165 and spring shelf upstand 166, cap lid 172 and the wall of cage body 161 on one side of the implant module, and the first arm 138 of the spring 105 of the second adjacent implant module 101 is enclosed by a spring shelf 165 and spring shelf upstand 166, cap lid 172 and the wall of cage body 161 on the other side of the implant module 101.

A desired amount of pre-loading can now be separately applied to each vertebra by the use of tensioners 107. Each tensioner 107 is inserted into cap aperture 174, and the tensioner shaft 176 engages with the tensioner engagement means in the cap shaft aperture 174b. By engaging a tool with tensioner tool cavity 177, tensioner 107 is manipulated into the correct position, in which tensioner crown 175 is surrounded by cap lid aperture 174a. In an active implant module (such as is as shown in FIG. 3), the end of tensioner shaft 176 abuts the centre of spring 105 inside spring socket 104. This causes tension to be applied to the implant module 101 relative to the first adjacent implant module and the second adjacent implant module via the spring 105, providing for a translation of the first vertebra relative to the first adjacent vertebra and the second adjacent vertebra. As will be appreciated by one skilled in the art, the amount of tension applied depends on the characteristics of spring 105, and also on the length of tensioner shaft 176, as the amount of force applied to the centre of spring 105 will depend on how far tensioner shaft 176 extends beyond cap shaft aperture 174b. In some cases, the desired tension may be achieved by having a tensioner shaft 176 of a length that does not extend beyond cap shaft aperture 174b at all.

The tension of each individual implant module can be adjusted until the correct desired amount of pre-loading is applied to each separate vertebra, according to the clinical needs of that patient to achieve the desired correction and freedom of movement.

Alternatively, the tensioner 107 can be omitted, and the force applied by each spring can be adjusted by altering the type of spring used e.g. by using a thicker spring if a greater force is required, or a thinner spring if less force is required. Alternatively, or additionally, the force applied by each spring can be adjusted by altering the height above the spine of the corresponding spring shelf 165, by varying the proportions of the cage 102.

As clearly shown in FIG. 4a, each arm of each spring 105 is flexed upwards to engage the corresponding spring shelf 165 of the adjacent module. This flexion preloads each spring such that each module exerts a lifting force on the vertebra to which is attached. This lifting force is applied along the longitudinal axis Y-Y of each module, and experiment has found that this lifting movement, in combination with the rotating movement applied by the interconnection between the modules as described below, together applies a straightening force on the distorted portion of the spine to which it is applied.

The rotating movement is provided by the manner in which each spring is connected to each adjacent module; the shape and the material of each spring means that the springs are resilient, and when each end of each spring is engaged with the corresponding spring shelf 165 of the adjacent module, the overall effect is not only to apply a force on the axis Y-Y of the corresponding module, but also to apply a rotary force about the same axis, as indicated by arrow A in FIG. 4b.

The direction of the rotary force can be reversed by engaging each arm of each spring with the opposing spring shelf 165 of the adjacent module. Thus, referring to FIG. 4b, arms 138a-138e inclusive are shown as engaged with spring shelves 165a-e inclusive; arms 139 are engaged with the opposite spring shelves; this overall gives a rotational movement in the direction of arrow A. However, if each of the arms 138a-138e is instead engaged with the opposing spring shelf 165f-165k, and the arms 139 are engaged with the spring shelves 165a-e, a rotational force in the opposite direction will be applied.

The selection of the degree of lifting and rotational forces to be applied by the apparatus, and direction of the rotational force, are selected by the surgeon, as appropriate to the requirements of the particular patient concerned.

It will be noted that when the springs of a series of modules are installed as shown in FIG. 4a/b the arms of the springs of adjacent modules extend alongside each other; this not only provides a stable, balanced system but also gives the necessary force along the axis Y-Y of each module.

The above described apparatus is fitted to a patient by being inserted under the skin over the spine. However, the apparatus of the present invention is significantly less intrusive to install than a majority of existing devices. This is an important advantage, because it has been found experimentally that if the periosium is unduly disturbed when fitting any apparatus, this can encourage spinal fusion, which of course is undesirable if a normal range of movement of the spine is to be retained. After all the implant modules 101 have been installed and adjusted, the implant modules 101 are covered by tissue and skin.

The intent of this system is that only a "gentle" straightening force would be applied to the vertebral bodies rather than the application of large forces as is currently required in order to realign the spine with standard spinal implants. Thus, in a similar way to which braces work in orthodontics, these gentle forces would over time cause "realignment" of the vertebral bodies.

The implant modules 101 continue to apply forces to each vertebra based on the pre-load of its associated spring 105 over time following surgery. Rather than an immediate total correction, there is a gradual improvement in spinal alignment over time. As the spine nears the desired alignment, the springs 105 approach their rest state and the forces exerted by the implant modules 101 decreases, limiting the risk of over-correction. Although in some cases it may be desirable to readjust some of the implant modules after surgery, it is hoped that in most cases this will not be necessary. It may eventually be possible to remove the units from the spine, which has adjusted to its new position.

Second Preferred Embodiment

Figure 5:
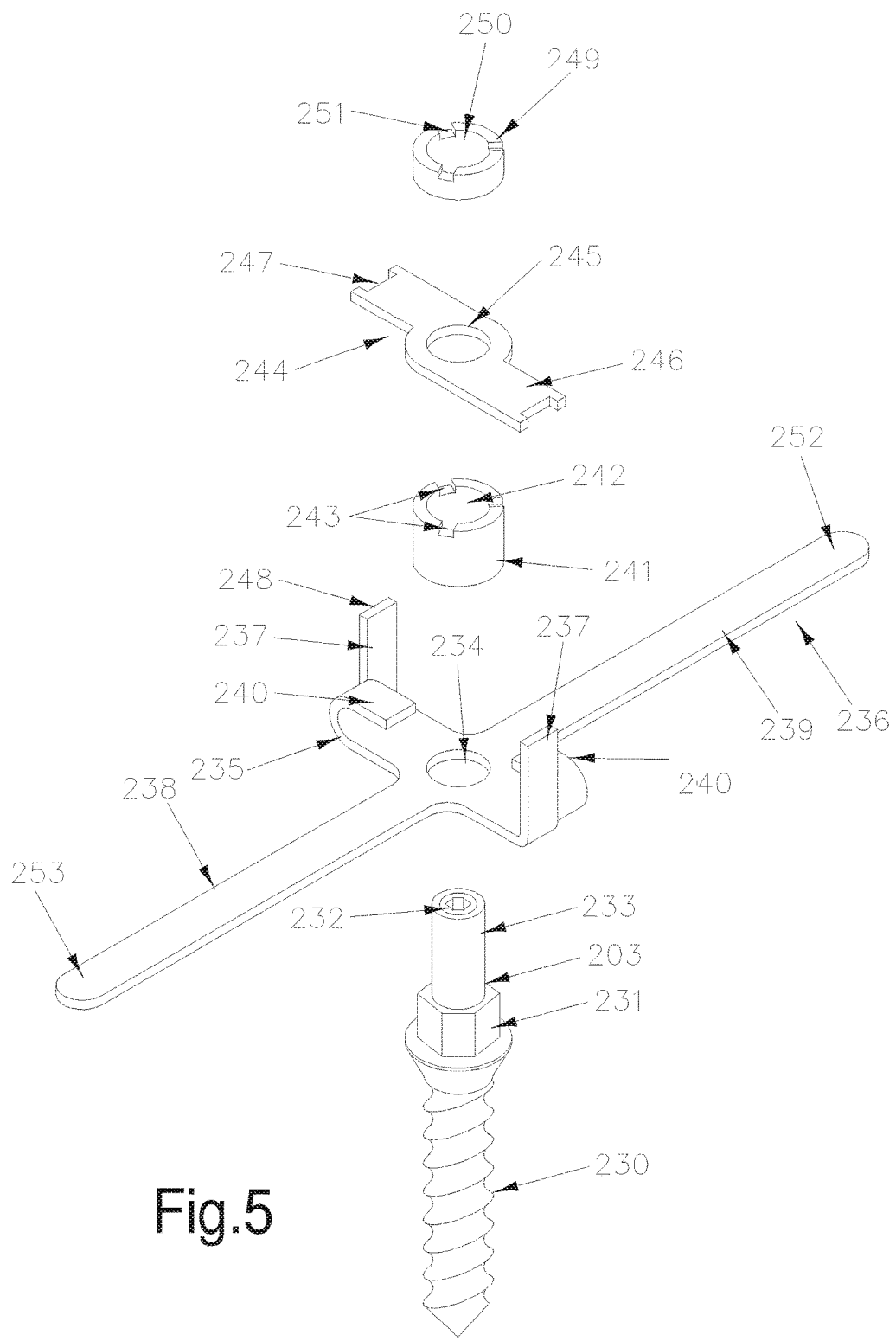
FIG. 5 is an exploded perspective view of a second embodiment of an implant module of the present invention.
Figure 6:
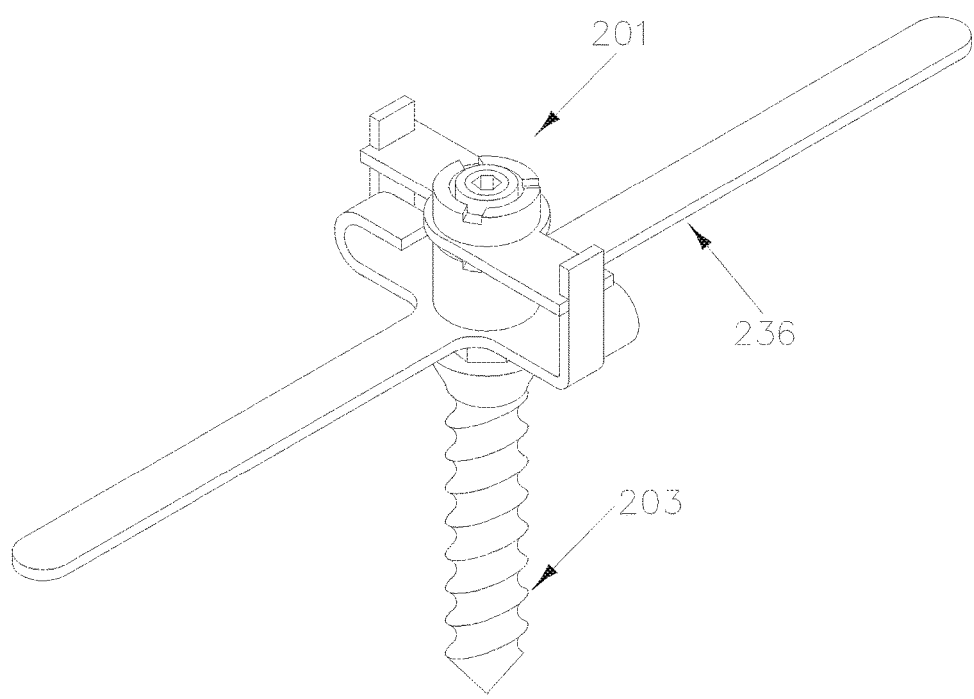
FIG. 6 is an isometric view of the implant module shown in FIG. 5 when assembled.

FIG. 5 and FIG. 6 show two different views of a second embodiment of an implant module 201 which is a part of the apparatus of the present invention.

The implant module 201 includes a pedicle screw 203, similar to a well-known type including a screw threaded column 230 adapted to engage with a pedicle of a vertebra. The column 230 is co-axial with a screw-threaded shaft 233. To allow for screwing the screw 203 into a pedicle, tool engagement means may be provided on or adjacent the shaft 233. These tool engagement means may include external flats 231 and/or a screw tool cavity 232 adapted to receive a tool, e.g. an Allen key. Engagement of an appropriate known type of tool with either of these tool engagement means will allow rotation of the screw 203, and therefore engagement of column 230 with a pedicle.

Screw 203 may be similar to any of the many different commercially available spinal screws. In alternative embodiments, the pedicle screws 203 may be replaced with "pedicle hooks" or other known apparatus for engagement with vertebrae the spine. Instead of the fixed angle screw illustrated, a multi-axial screw may be used, to help facilitate alignment.

Implant module 201 further includes a spring 236, which includes a first arm 238 and a second arm 239 aligned in a spring plane. Near the centre of spring 236 a spring hole 234 is dimensioned to allow the shaft 233 of screw 203 to pass therethrough. On either side of spring hole 234 is formed a spring wing 235 which includes an upstand 237 extending approximately perpendicular to the spring plane. Each spring wing 235 further includes a shelf 240 which is approximately parallel to the spring plane, but displaced therefrom. Each shelf 240 extends towards, but does not block, the spring hole 234. Although springs 236 are shown as leaf springs, other forms could be used, such as flexible rods or bars, or contoured and profiled forms, and may be of varying thickness and cross-section.

A spring cap 241 is an essentially annular spacer having an internal screw threaded spring cap hole 242 adapted to engage with the shaft 233 of the screw 203. Spring cap 241 may also include tool engagement means such as internal/external cap tool cavities 243.

A spring retainer 244 includes a retainer hole 245 of similar dimension to spring cap hole 234 and two retainer wings 246. Each retainer wing 246 is slightly longer than a corresponding spring wing 235, and includes a notch 247 dimensioned to receive an end 248 of an upstand 237. In the embodiment shown, each retaining wing 246 is offset from the other, to match the corresponding offset of each upstand 237.

A lock nut 249 is an essentially annular nut having an internal screw threaded nut hole 250 adapted to engage with the shaft 233 of the screw 203. Lock nut 249 may also include tool engagement means such as nut tool cavities 251.

It will be recognised by one skilled in the art that the implant modules must be made of appropriate surgical materials, having the necessary characteristics of ability to be sterilized, biological inertness, strength and flexibility. In particular, different materials and spring geometries used for springs 236 will apply different strengths of spring force, as may be required in a particular case.

Implant modules 201 are used in the method of treatment of the present invention. Using known tools and techniques, screws 203 are screwed into the pedicles of vertebrae along the affected length of the spine. Screws 203 may be engaged with every vertebra, or Jo some may be skipped, depending on the extent of the scoliosis, patient condition, and the desired end result.

Once the screws 203 are in place, the springs 236 are sequentially installed. A spring 236 is lowered over pedicle screw 203 so that shaft 233 passes through spring hole 234. An end 252 of first arm 239 of spring 236 rests on a shelf 240 of an adjacent spring 236. On the other shelf 240 of said adjacent spring rests an end 253 of the second arm 238 of a further spring 236, so that (other than for the two end implant modules), for each implant module 201 the end 252 of first arm 239 and the end 253 of second arm 238 of the spring 236 rest on the shelves 240 of different adjacent springs 236. This engagement of the arms 238, 239 and their ends 252, 253 with the shelves 240 may occur as each spring 236 is added, or after all the springs are in place.

It will be appreciated that implant modules 201 may be supplemented by similar end implant modules (not shown) wherein the spring has only one arm to engage with a spring of a single adjacent implant module. When implant modules 201 are not to be installed in every adjacent vertebra, springs 236 may have arms of different lengths, to reach the shelves 240 of the next adjacent springs.

The spring cap hole 242 of a spring cap 241 is aligned with shaft 233 and screwed into place for each implant module 201. The amount of pre-load on each spring 236 is determined by the spacing between the underside of spring cap 241 and column 230 of the pedicle screw 203. As the centre of spring 236 is displaced with respect to its neighbouring springs 236, the arms 238, 239 of the spring 236 flex, resulting in a force being exerted along the axis of the pedicle screw 203, and subsequently on a connected vertebra of the spine.

At this stage, the amount of pre-loading on each spring 236 is adjusted according to the desired end result, by appropriate tightening of the spring caps 241 during surgery. The amount of freedom of movement to be allowed the patient can also be selected by variations in the tightness of spring caps 241, or by use of spring caps of various heights. A coarser adjustment may also be effected by altering the length of the screw 203 which is screwed into the corresponding vertebra; this alters the height of the corresponding to shelves 240, and thus alters the forces exerted by the spring 236.

Once the spring cap 241 has been appropriately adjusted, spring retainer 244 is fitted by passing shaft 233 through the retainer hole 245 and aligning the notch 247 in each retainer wing 246 with a corresponding upstand 237 of that spring 236. Lock nut 249 is then screwed into place on the top of shaft 233 to hold spring retainer 244 in place. Once spring retainer 244 is in place, an end 253, 252 of each arm 238, 239 of adjacent springs 136 is contained within a "cage" bounded by a shelf 240 on the bottom, spring cap 241 to one side and upstand 237 on the other, and on the top by a retainer wing 246 of spring retainer 244. This limits the risk of a spring disengaging from its neighbour as the patient moves, which would result in a change in the spring force applied by that spring.

Third Embodiment

Figure 7:
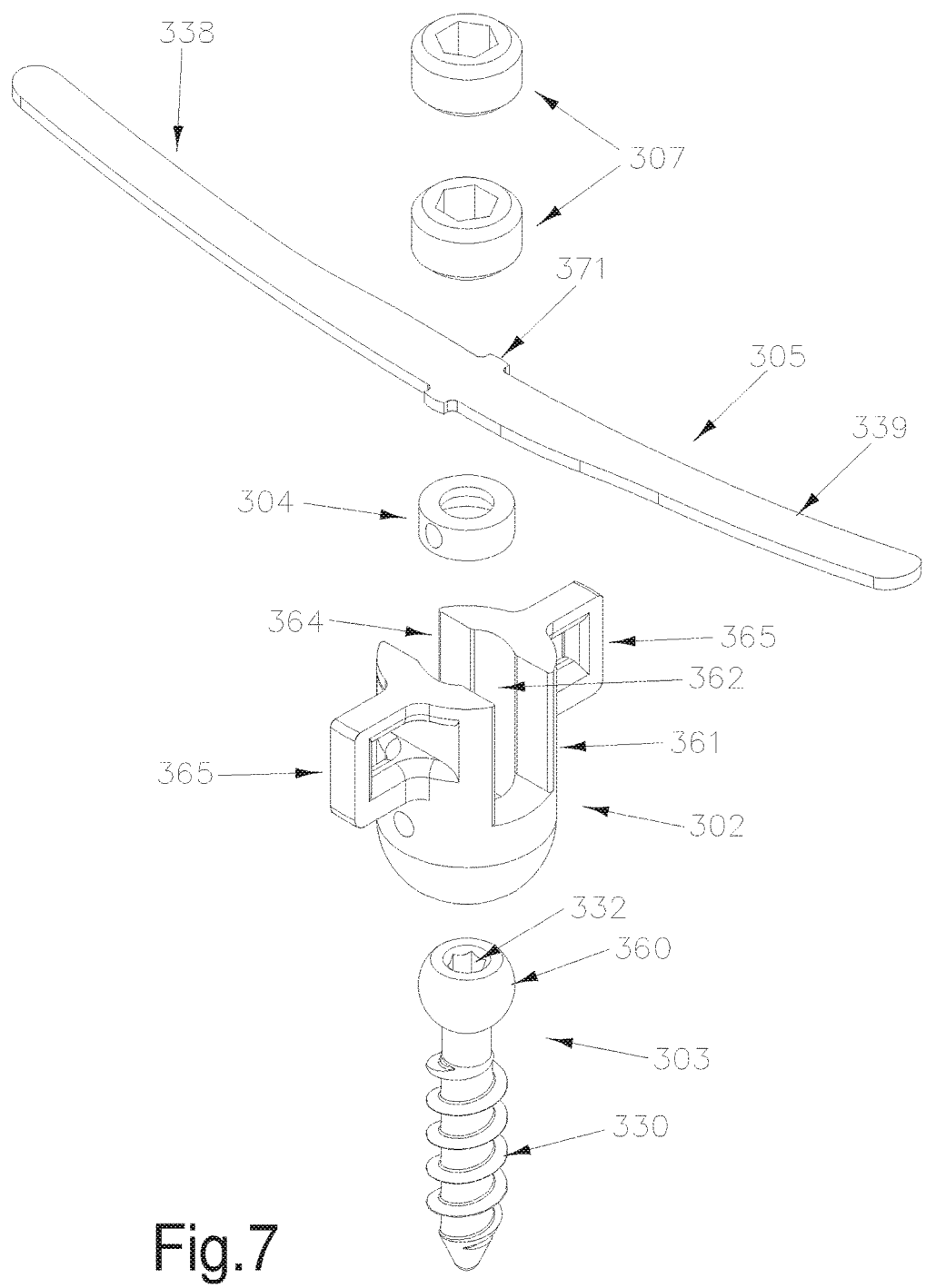
FIG. 7 is an exploded isometric view of a third embodiment of an implant module of the present invention.
Figure 8:
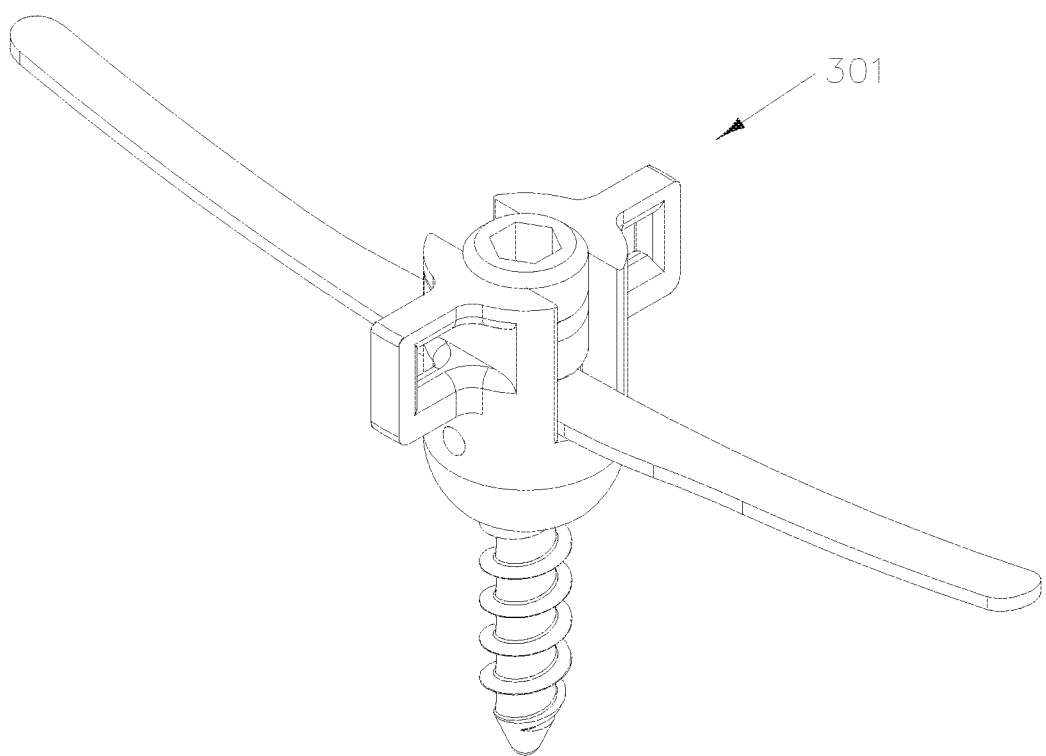
FIG. 8 is an isometric view of the implant module shown in FIG. 7 when assembled.

FIG. 7 and FIG. 8 show two different views of a third embodiment of an implant module 301 which is a part of the apparatus of the present invention.

The implant module 301 includes a cage 302, a pedicle screw 303, a spring socket 304, spring 305, and connection means 307. Pedicle screw 303 includes a screw threaded column 330 adapted to engage with a pedicle of a vertebra. At a first end of column 330, a rounded screw head 360 is provided with tool engagement means, preferably in the form of a screw tool cavity 332 adapted to receive a tool, e.g. an Allen key.

Cage 302 has an essentially cylindrical cage body 361, with a central bore 362 dimensioned such that screw threaded column 330 of pedicle screw 303 passes therethrough and the screw threaded column 330 extends from a first end of the cage body 361, but the rounded screw head 360 is retained within the bore 362 of the cylindrical cage body 361.

The sidewall of the cage body 361 includes two cage spring slots 364 opposite each other, each cage spring slot 364 extending from a second end of cage body 361 through a significant depth of the cage body side wall. Extending outwards from opposite sides of cage body 361 are a pair of spring engagement means 365, each of which is equidistant from the two cage spring slots 364. In this embodiment the spring engagement means 365 are closed loops, each configured to retain one arm 338, 339 of a leaf spring 305 of an adjacent implant module.

Figure 9:
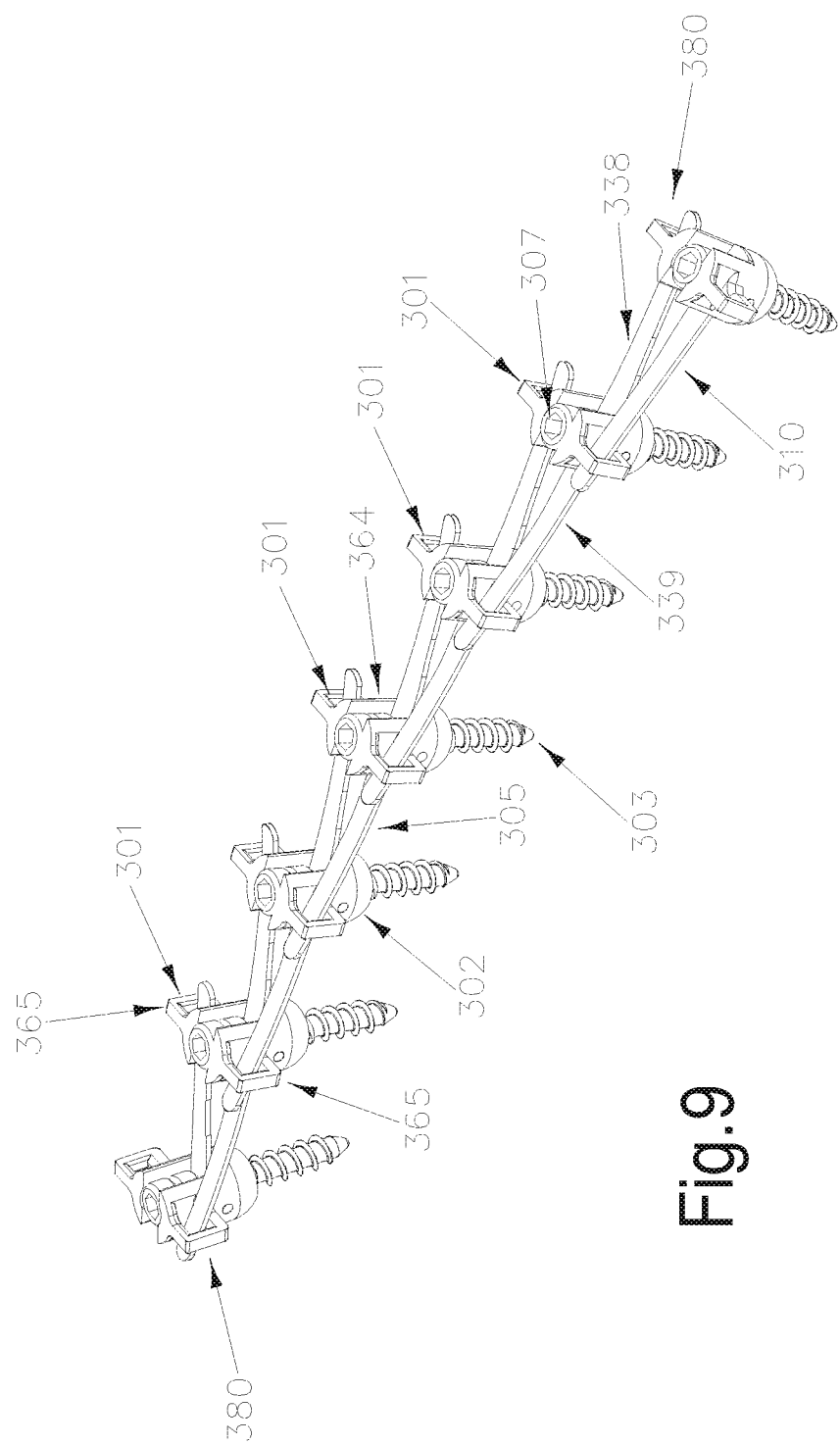
FIG. 9 is an isometric view of a third embodiment of a series of implant modules according to the present invention.
Figure 10:
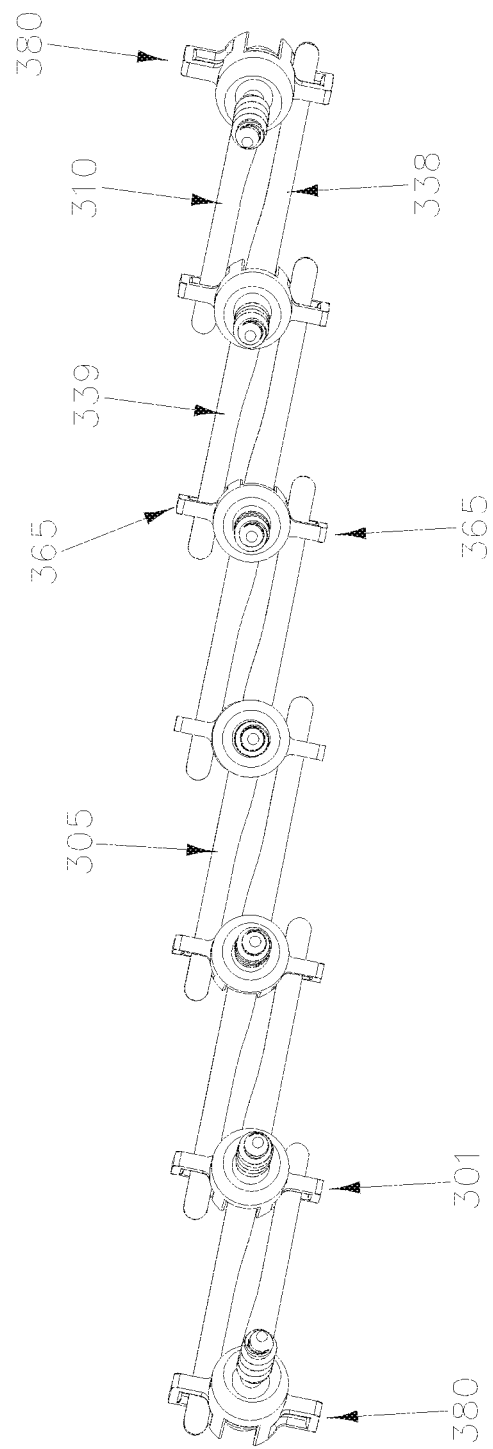
FIG. 10 is a bottom view of the implant modules shown in FIG. 9

Leaf spring 305 is placed in the cage body 361, crossing the central bore 362, and is retained via adjustable connection means 307. A first arm 338 and a second arm 339 of the leaf spring 305 each extend through a cage spring slot 364. A pair of small opposing protrusions 371, located partway along the leaf spring 305, engage with an interior wall of the bore 362, limiting lengthwise translation of the leaf spring 305. The adjustable connection means 307 may be at least one screw threaded block engaged with a screw threaded section of the central bore 362 of the cage body 361. The connection means 307 also include tool engagement means to allow the engagement of the connection means with the central bore 362.

Where scoliosis affects a section of n vertebrae in a spine, the apparatus consists of at least n intermediate units 301 and two end units 380, as shown in FIGS. 9 and 10. Each end unit 380 is identical to an intermediate unit 301, except that an end spring 310 is a little over 50% of the length of a leaf spring 305, and is connected to cage 302 at a first end.

The apparatus is implanted in a scoliosis affected spine by attaching one intermediate unit 301 to a pedicle of each affected vertebra, along one side of the affected length of spine, and an end unit 380 to a pedicle of each of one vertebra above the affected length of spine and one vertebra below the affected length of spine.

Screws 303 may be engaged with every vertebra, or some may be skipped, depending on the extent of the scoliosis, patient condition, and the desired result. To implant a unit, screw 303 is inserted through cage 302 and screwed into a pedicle of the desired vertebra. In practice, screw 303 may be assembled with cage 302 and spring socket 304 installed in the central bore 362 above the screw head 360 before surgery commences, that is, these parts may be supplied as a pre-assembled unit. Once cage 302 has been attached to the vertebra by screw 303, leaf spring 305 (or end spring 310 in the case of an end unit 380) is inserted into cage 302 so that the first and second arms 338, 339 of the spring 305 extend through the cage spring slots 364. Connection means 307 are inserted into place in the central bore 362 to retain the leaf spring 305 in place.

Once the units have been implanted, an end spring 310 of an end unit 380 engages a spring engagement means 365 of an adjacent intermediate unit 301. First arm 338 of leaf spring 305 of said intermediate unit 301 engages a spring engagement means 365 of said end unit 380. Second arm 339 engages a spring engagement means 365 of a subsequent intermediate unit 301. This progression repeats along all the units, as shown in the drawings, so that each leaf spring 305 of an intermediate unit 301 engages spring engagement means of two adjacent units, and each end spring 310 engages the spring engagement means of one adjacent intermediate unit 301. As shown, spring engagement means 365 are loops, to securely engage the spring ends. However, spring engagement means 365 could be in any appropriate form, including (but not limited to) L-shaped brackets, straight or shaped protrusions, grooves or recesses.

To create curvature, and thus tension, in the springs 305, 310, connection means 307 are adjusted. In this embodiment, screwing the block into the unit, towards screw 303, curves the centre of leaf spring 305 relative to its ends. Adjusting the connection means 307 of an intermediate unit 301 so that leaf spring 305 forms an spinewards arc between the spring engagement means 365 of the adjacent units imposes a force on cage 302 of the intermediate unit 301, which is transferred to screw 303, and thus to that vertebra. A coarser adjustment may also be effected by altering the distance by which screw 303 is inserted its vertebra, which will alter the height of the corresponding spring engagement means 365, and thus alter the degree of force applied by the corresponding spring.

Thus, the adjustment of connection means 307 can be used to tune the force to be applied to each vertebra, depending on its location in the scoliosis-affected spine. Different strengths and types of spring can be used, depending on the desired force to be applied. The adjustment of connection means 307 allows fine tuning of the applied force, by affecting the amount of curvature in each spring.

As the vertebral bodies start to become "realigned" the springs will straighten, reducing the spring force applied to the vertebral bodies thus helping to prevent over correction of the scoliosis deformity. It may further be possible to vary the tension applied by the adjustment means 307 in subsequent operations, to apply appropriate force to each vertebra as the spine adjusts. It may eventually be possible to remove the units from the spine, which has adjusted to its new position.

Although springs 305, 310 are shown as leaf springs, other forms could be used, such as flexible rods or bars, or contoured and profiled forms and may be of varying thickness and cross-section.

Fourth Embodiment

Referring to FIGS. 11 to 14, two variants of a fourth embodiment are shown.

Figure 11:
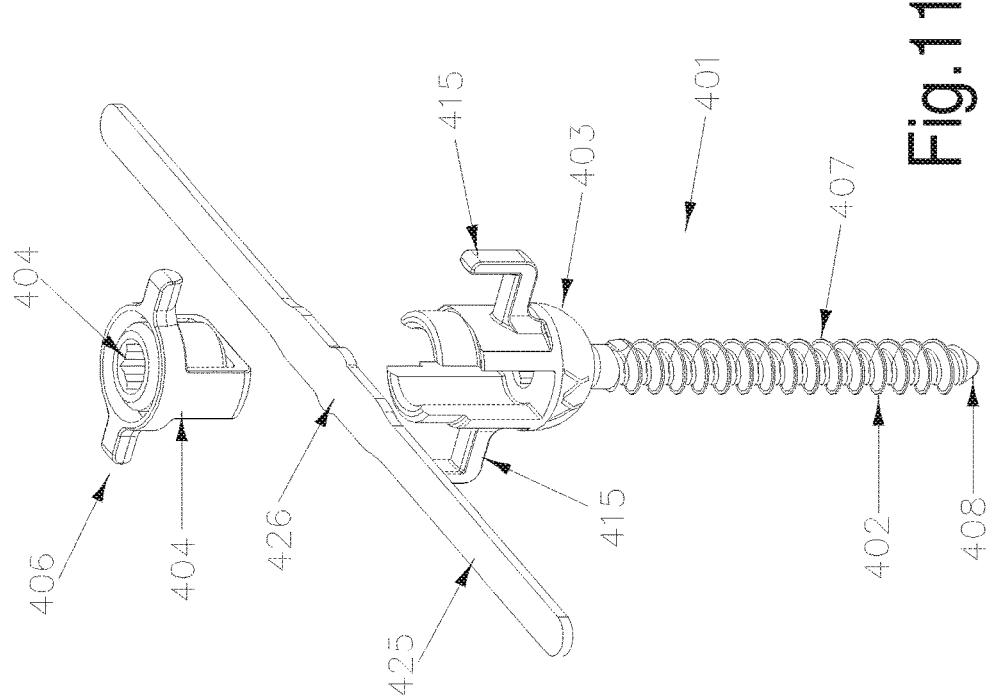
FIG. 11 is an exploded isometric view of a fourth embodiment of an implant module according to the present invention.

FIG. 11 shows an exploded isometric view of an implant module 401 which includes a pedicle screw 402 the upper end of which is formed integrally with the base of a cage 403; a reinforcing sleeve 404 is dimensioned to be a sliding fit over the exterior of the cage. The interior of the cage is screw threaded (not shown) to engage the screw threaded exterior of a retainer 406.

The pedicle screw 402 is of any of a range of known types and sizes of pedicle screw and provides a screw threaded exterior surface 407 from the lower end 408 to just below the point at which the screw is secured to the cage 403. The dimension and type of screw thread can be varied as required for particular applications.

In an alternative construction, rather than forming the pedicle screw integrally with the cage, the screw is formed separately and then the screw is rigidly secured to the base of the cage 403 by inserting the screw into an aperture through the base and then peening the head of the screw to hold the screw rigidly in position in the cage.

The cage 403 provides a tulip shaped body portion 409 having a base 410 and a pair of opposed part cylindrical sides 411, spaced apart by two opposed gaps 412. The inner surface of each of the sides 411 is formed with a screw thread 413 and the exterior surface of each of the sides 411 is formed with a shallow shoulder 414 on which part of the reinforcing sleeve 404 rests when the parts are assembled as described below.

Each of the sides 411 supports an L-shaped bracket 415, each of which consists of a first portion 416 the longitudinal axis of which is substantially perpendicular to the longitudinal axis A-A of the cage, and a second portion 417 the longitudinal axis of which is perpendicular to that of the first portion 416, such that each bracket 415 in combination with the corresponding side 411 provides a three sided support open at its upper end 418.

The reinforcing sleeve 404 provides an annulus 420 which is dimensioned to be an easy sliding fit over the exterior of the top of the cage 403, but to have a smaller interior diameter than the exterior diameter of the shoulder 414, so that when the reinforcing sleeve 404 is slid over the top of the cage 403 as shown in FIG. 15, the annulus rests on the shoulder 414.

The reinforcing sleeve also provides a U-shaped yoke 421 formed integrally with the annulus 420 and dimensioned such that each side 422 of the yoke is an easy sliding fit in the corresponding gap 412 in the side of the cage. The reinforcing sleeve further provides a pair of diametrically opposed projections 423 which extend one on each side of the annulus 420 and are positioned and dimensioned such that when the reinforcing sleeve is positioned over the cage 403 as shown in FIG. 11, each projection 423 extends over the corresponding L-shaped bracket 415 to close off at least part of the upper end 418 (see FIG. 15).

As shown in FIG. 12a, a spring 425 comprises an elongated flat leaf spring, the central portion 426 of which is enlarged in width compared to the rest of the spring; the diameter of the portion 426 is less than the internal diameter of the cage 403, but slightly greater than the width of the gaps 412. Thus, the spring 425 can be mounted in the cage with the portion 426 located in the centre of the cage, and once the reinforcing sleeve 404 and the retainer 406 are inserted, and the retainer 406 is screwed into engagement with the screw thread 413, the spring 425 is secured in position in the cage.

The retainer 406 is an externally screw threaded cylinder with an internal bore 427 which is shaped to receive a driving tool such as a screwdriver or an Allen key. The base of the retainer 406 is formed with a short central projection 428 which is dimensioned to engage a corresponding aperture 429 in the base of the yoke, to centre the retainer in the yoke.

Screwing the retainer 406 into engagement with the screw thread 413 presses the base of the yoke 421 tightly against the central portion 426 of the spring 425, securing the spring in position. The enlarged diameter of the portion 426 prevents the spring 425 from slipping sideways out of the cage 403.

The above described module is used as follows: each pedicle screw 402 is screwed into a vertebra at the position selected by the surgeon by inserting a tool into the screw threaded interior 413 of the cage 403, which is rigidly secured to the pedicle screw. Once the pedicle screw and cage are correctly positioned, the spring 425 is positioned in the cage 403 as described above and is held in position by the reinforcing sleeve 404 positioned over the cage. The components are then secured together by screwing the retainer 406 into the screw thread 413 of the cage 403.

Figure 13:
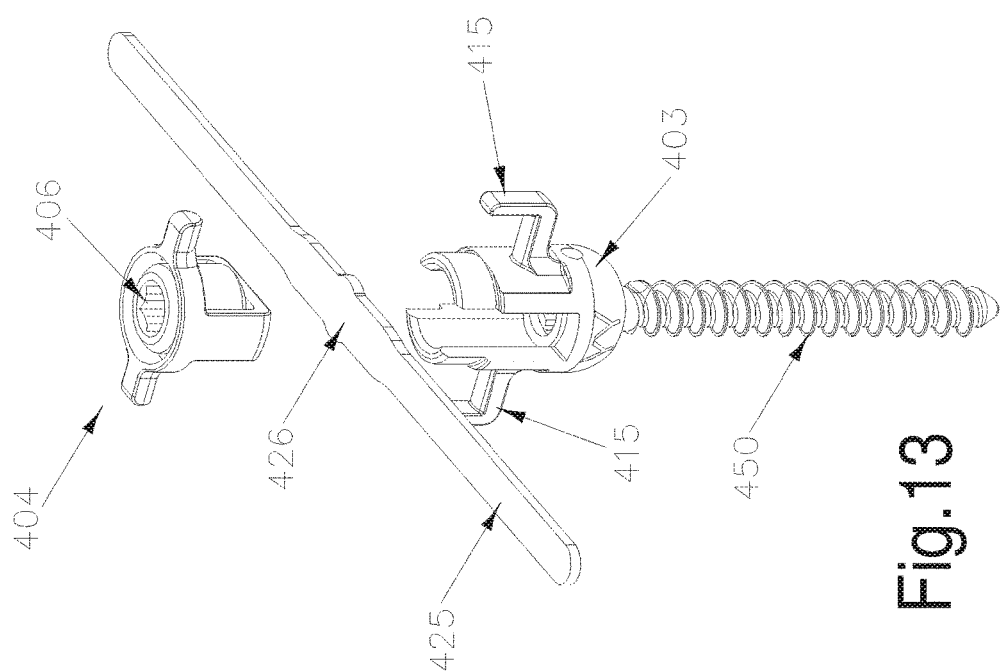
FIG. 13 is an exploded isometric view of a variant of the embodiment of FIG. 11.
Figure 11A:
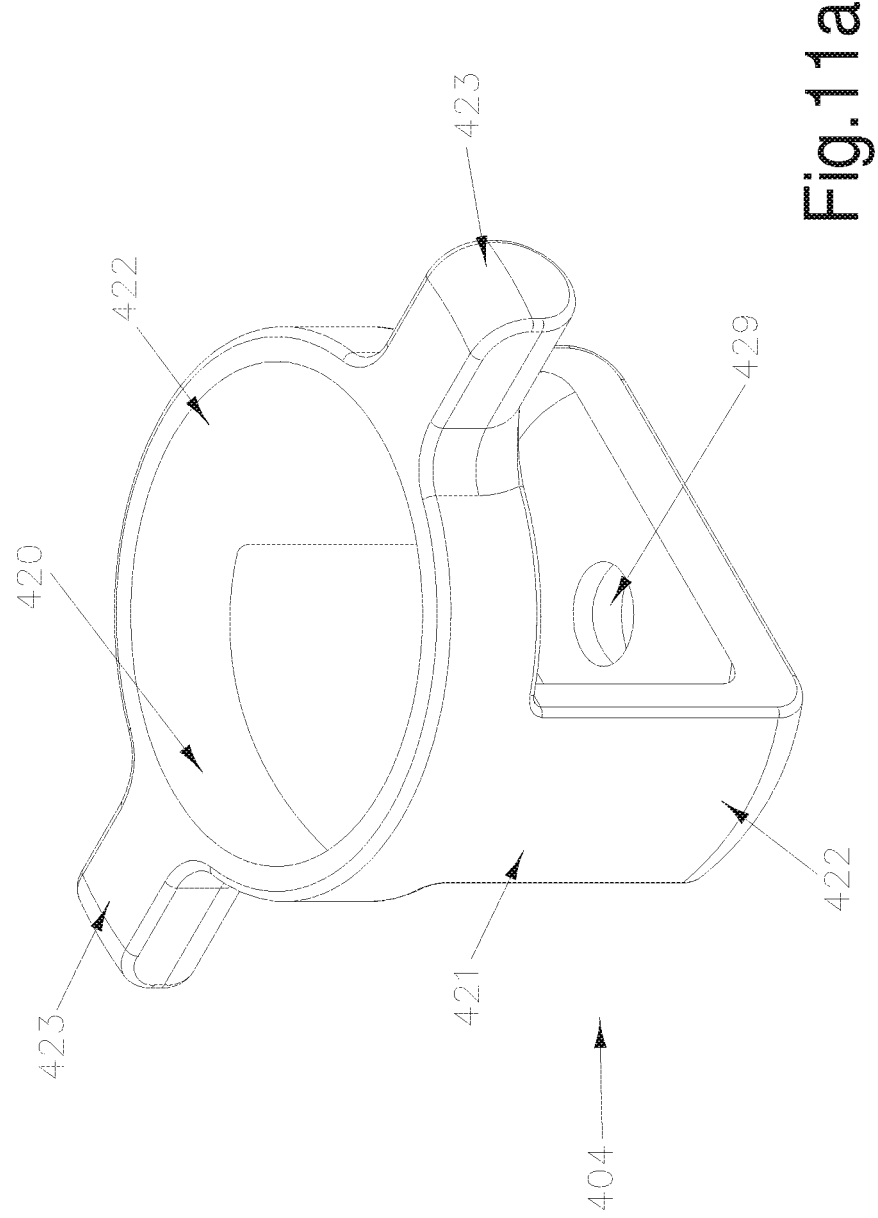

A variant of the above described implant module is shown in FIGS. 13 and 14. The only difference is the connection between the pedicle screw and the cage; in the variant of FIGS. 13 and 14, the pedicle screw 450 is formed with an enlarged part spherical head 451 which is dimensioned to fit within a complimentary part spherical aperture (not visible) in the base of the cage, so that the pedicle screw can rotate relative to the cage through an angular range of approximately ±15°.

This variant is used where access to the desired part of a vertebra is difficult, and it is advantageous to be able to set the pedicle screw with the longitudinal axis of the pedicle screw at an acute angle to the longitudinal axis of the cage; it may also assist in assembling the modules together when dealing with severe deformity.

The head 451 of the pedicle screw is formed with a drive socket 452 for a suitable driving to tool (e.g., screwdriver, Allen key) and once the pedicle screw has been screwed into the desired position, it can be locked in that position relative to the cage by positioning the spring, reinforcing sleeve and retainer as described above and screwing the retainer down onto the base of the reinforcing sleeve yoke to press the yoke into tight engagement with both the spring and the underlying head 451 of the pedicle screw, locking both in position.

In the fourth embodiment, the degree of force exerted by the springs is altered by altering the springs themselves; the width and/or thickness of the springs is varied as necessary to provide the required degree of force. In addition, as with the previous embodiments, the force may also be adjusted by altering the amount by which the pedicle screws are screwed into the corresponding vertebrae, to alter the height of the brackets 415. Both variants of the fourth embodiment are installed in the same manner as described with reference to the first three embodiments; once each pedicle screw has been installed and each spring positioned in the corresponding cage, the or each end of each spring is engaged with the corresponding bracket 415 as shown in FIG. 15.

FIG. 15 shows a short section of apparatus with end implant modules 500 and 506, both of which have only a single ended springs, 501 and 510 respectively. From the implant module 500, a single ended spring 501 is engaged with the bracket 502 on the next implant module 503. The implant modules 503, 504, and 505 have double ended springs 507-509 inclusive.

As shown in FIG. 12B, the single ended spring 501, 510 has a single end, but has the same larger diameter mid-portion 426 as the double ended spring. The single ended springs are used only with the end implant modules, as shown in FIG. 15.

As with the previously described embodiments, the or each arm of each spring is flexed upwards to engage the corresponding spring shelf of the or each adjacent module (s). This flexion preloads each spring such that each module exerts a lifting force on the vertebra to which it is attached. This lifting force is applied along the longitudinal axis Y-Y of each module, and experiment has found that this lifting movement, in combination with the rotating movement applied by the interconnection between the modules as described above, together applies a straightening force on the distorted portion of the spine to which it is applied.

The rotating movement is provided by the manner in which each spring is connected to each adjacent module:— the shape and the material of each spring means that the springs are semirigid but resilient and when the or each end of each spring is engaged with the corresponding spring shelf of the adjacent module, the overall effect is not only to apply a force on the axis Y-Y of the corresponding module, but also to apply a rotary force about the same axis, as indicated by arrow A in FIG. 15.

The direction of the rotary force applied can be reversed as described with reference to the first embodiment.

As with embodiments 1-3, as shown in FIG. 15, when the springs of the modules are installed as described above, the arms of the springs of adjacent modules extend alongside each other to provide a stable, balanced system and to give the necessary force along the axis Y-Y of each module.

Figure 15A:
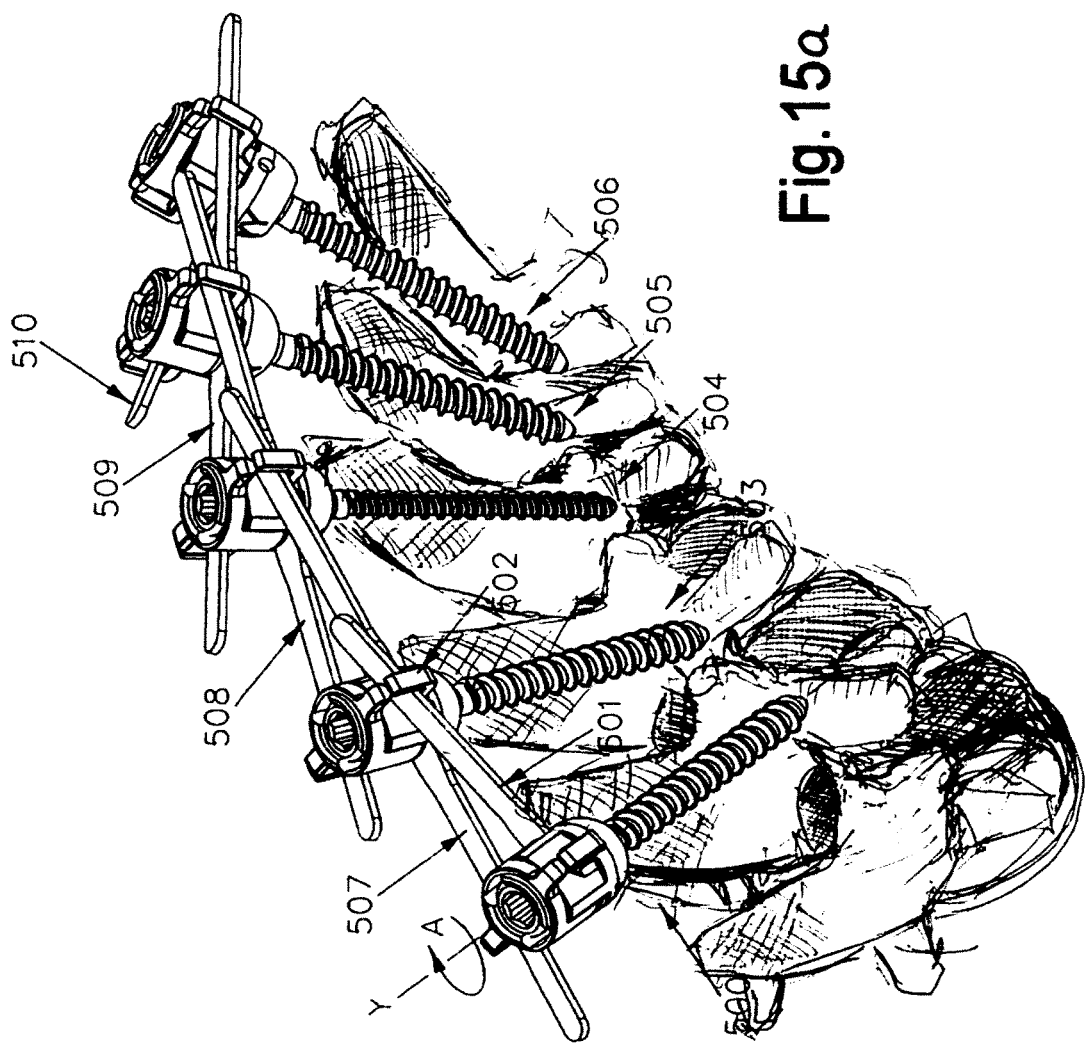
FIG. 15a an isometric view as in FIG. 15, showing the implant modules engaged with vertebrae (sectioned).

The apparatus described with reference to the fourth embodiment is inserted into a patient in the same manner as described with reference to the first embodiment, and operates in the same manner to apply a correcting force to the spine. FIG. 15a shows (diagrammatically) the modules of FIG. 15 engaged with a series of vertebrae, shown partially sectioned.

It is emphasised that all of the embodiments described above provide modules which interact with each other in a substantially identical manner; in each embodiment, the or each arm of each spring is flexed upwards to engage the corresponding spring shelf of the adjacent module, and this flexion preloads the spring such that each module exerts a lifting force on the vertebra to which it is attached. As described above, this lifting force is applied along the longitudinal axis of each module. It addition, each apparatus provides a rotating movement by virtue of the manner in which each spring is connected to each adjacent module, as described above. In all of the embodiments, the direction of this rotary force can be reversed if necessary, as described with reference to the first embodiment.

In all of the above described embodiments, each end of each spring can slide in the plane of the spring relative to the bracket with which it is engaged on an adjacent module, such that the spring secured to each module can slide relative to adjacent modules as the curvature of the spine alters. This ensures that the assembled modules continue to apply a corrective force on the spine throughout the correction process.

What is claimed is:

1. A spinal adjustment system which includes at least three implant modules, wherein each implant module includes:
    an engagement apparatus for engaging the implant module with a vertebra; and
    a semirigid, resilient elongated force application means which in use is secured to said engagement apparatus and extends from one implant module to the or each adjacent implant module;
wherein:
    said force application means in use engages said the or each adjacent implant module such that said force application means can slide relative thereto in the plane of the force application means;
    each force application means in use applies a lifting force to the corresponding implant module and said at least three implant modules together in use apply a rotational force to said system; and
    the force application means extending from one implant module to an adjacent implant module extends alongside the force application means extending from said adjacent implant module to said one implant module.

2. The spinal adjustment system as claimed in claim 1, wherein the engagement apparatus for engaging each implant module with the corresponding vertebra is selected from the group consisting of: pedicle screws, pedicle hooks.

3. The spinal adjustment system as claimed in claim 1, wherein the force application means is selected from the group consisting of: a leaf spring, a rod, a bar.

4. The spinal adjustment system as claimed in claim 1, wherein the force applied by each force application means is adjustable by altering the dimensions and/or proportions of the force application means.

5. The spinal adjustment system as claimed in claim 4, wherein the force applied by each force application means is also adjustable by a spring tensioner.

6. The spinal adjustment system as claimed in claim 1, wherein said engagement apparatus is a pedicle screw which is rigidly secured to a cage for receiving and supporting said force application means.

7. The spinal adjustment system as claimed in claim 1, wherein said engagement apparatus is a pedicle screw which is pivotably secured to a cage for receiving and supporting said force application means, and wherein said system further includes means for locking the angle between said pedicle screw and said cage.

8. An implant module for use in the spinal adjustment system as claimed in claim 1, wherein said implant module includes:
    an engagement apparatus for engaging the implant module with a vertebra;
    a semirigid, resilient elongated force application means which in use is secured to said engagement apparatus and is arranged to extend outwards from said module so as to be engageable with an adjacent module; and
    a pair of opposed receiving means each arranged to slidably receive an end of said force application means.

9. The implant module as claimed in claim 8, wherein said engagement apparatus is selected from the group consisting of: pedicle screws, pedicle hooks.

10. The implant module as claimed in claim 8, wherein the force application means is selected from the group consisting of: a leaf spring, a rod, a bar.

11. The implant module as claimed in claim 8, wherein said engagement apparatus is rigidly or pivotably secured to a cage for receiving and supporting said force application means, said cage having said pair of opposed receiving means rigidly secured thereto.

12. The implant module as claimed in claim 11, wherein said cage is internally screw threaded and is formed with a pair of opposed slots dimensioned such that said force application means is receivable within said cage with at least one end of said force application means extending outwards from said module; and wherein said module further includes a reinforcing sleeve which is dimensioned to be an easy sliding fit over said cage and provides a U shaped yoke having side portions positioned and dimensioned to close off said opposed slots, and a base portion which overlies the portion of said force application means within said cage.

13. The implant module as claimed in claim 12, further including a retainer formed with an internal bore for receiving a driving tool, said retainer being externally screw threaded to engage the internal screw thread on said cage, such that when said retainer is screwed into the cage, the retainer, reinforcing sleeve, and force application means are rigidly secured together.

14. The implant module as claimed in claim 13, wherein said retainer provides a pair of opposed projections positioned so as to overlie said pair of opposed receiving means when said retainer is positioned on said cage.

15. The implant module as claimed in claim 8, wherein said engagement apparatus is a pedicle screw which is rigidly secured to a cage for receiving and supporting said force application means, said cage having said pair of opposed receiving means rigidly secured thereto.

16. A method of adjusting the alignment of a spine, including the steps of:
   providing a spinal adjustment system as claimed in claim 1;
   engaging each implant module with a vertebra in the part of the spine to be realigned, by means of said engagement apparatus;
   engaging the force application means of each implant module with the or each adjacent implant modules, such that each force application means applies a lifting force to the corresponding implant module, and said at least three implant modules together apply a rotational force to the associated part of the spine.

17. The use of the method as claimed in claim 16 for the treatment of a condition selected from the group consisting of: scoliosis, spondylolisthetic vertebra, Scheuermann's kyphosis.

* * * * *